United States Patent
Gleich et al.

(10) Patent No.: US 11,598,677 B2
(45) Date of Patent: Mar. 7, 2023

(54) TRACKING SYSTEM AND MARKER DEVICE TO BE TRACKED BY THE TRACKING SYSTEM

(71) Applicant: KONINKLIJKE PHILIPS N.V., Eindhoven (NL)

(72) Inventors: Bernhard Gleich, Hamburg (DE); Juergen Erwin Rahmer, Hamburg (DE); Michael Grass, Buchholz in der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 197 days.

(21) Appl. No.: 16/708,513

(22) Filed: Dec. 10, 2019

(65) Prior Publication Data

US 2020/0397510 A1    Dec. 24, 2020

(51) Int. Cl.
*A61B 5/00*      (2006.01)
*G01K 7/36*      (2006.01)
(Continued)

(52) U.S. Cl.
CPC .......... *G01K 7/36* (2013.01); *A61B 1/00158* (2013.01); *A61B 5/0215* (2013.01); *A61B 5/02152* (2013.01); *A61B 5/05* (2013.01); *A61B 5/062* (2013.01); *A61B 5/6851* (2013.01); *A61B 5/6852* (2013.01); *A61B 34/20* (2016.02);
(Continued)

(58) Field of Classification Search
IPC ............ A61B 34/20,90/36, 90/39, 5/05, 5/062, 5/6891
See application file for complete search history.

(56) References Cited

U.S. PATENT DOCUMENTS

| | | | |
|---|---|---|---|
| 6,129,668 A | 10/2000 | Haynor et al. | |
| 2002/0107445 A1* | 8/2002 | Govari | A61B 5/061 600/437 |

(Continued)

FOREIGN PATENT DOCUMENTS

| | | |
|---|---|---|
| WO | 03053533 A1 | 7/2003 |
| WO | 2008142629 A1 | 11/2008 |

OTHER PUBLICATIONS

Maxwell et al "Validation of the Calypso Surface Beacon Transponder", Journal of Applied Clinical Medical Physics, vol. 17, pp. 223-234 (2016).

*Primary Examiner* — Joel F Brutus
(74) *Attorney, Agent, or Firm* — Sherry Austin

(57) ABSTRACT

A tracking system for tracking a marker device for being attached to a medical device is provided, whereby the marker device includes a sensing unit comprising a magnetic object which may be excited by an external magnetic or electromagnetic excitation field into a mechanical oscillation of the magnetic object, and the tracking system comprises a field generator for generating a predetermined magnetic or electromagnetic excitation field for inducing mechanical oscillations of the magnetic object, a transducer for transducing a magnetic or electromagnetic field generated by the induced mechanical oscillations of the magnetic object into one or more electrical response signals, and a position determination unit for determining the position of the marker device on the basis of the one or more electrical response signals.

23 Claims, 16 Drawing Sheets

(51) Int. Cl.
  *G01K 1/26* (2006.01)
  *G01K 13/04* (2006.01)
  *A61B 5/0215* (2006.01)
  *G01L 9/00* (2006.01)
  *A61B 34/20* (2016.01)
  *A61B 90/00* (2016.01)
  *A61B 5/06* (2006.01)
  *A61B 1/00* (2006.01)
  *A61B 5/05* (2021.01)

(52) U.S. Cl.
  CPC ............ *A61B 90/36* (2016.02); *A61B 90/39* (2016.02); *G01K 1/26* (2013.01); *G01K 13/04* (2013.01); *G01L 9/0001* (2013.01); *G01L 9/007* (2013.01); *A61B 5/02158* (2013.01); *A61B 2034/2051* (2016.02); *A61B 2034/2072* (2016.02); *A61B 2090/3958* (2016.02); *A61B 2090/3966* (2016.02); *A61B 2562/0223* (2013.01)

(56) References Cited

U.S. PATENT DOCUMENTS

| | | |
|---|---|---|
| 2003/0004411 A1* | 1/2003 | Govari ............... A61B 17/1114 600/424 |
| 2003/0040670 A1* | 2/2003 | Govari .................. G01B 7/30 324/207.13 |
| 2003/0117269 A1 | 6/2003 | Dimmer |
| 2004/0019447 A1 | 1/2004 | Schachar |
| 2004/0129279 A1 | 7/2004 | Fabian et al. |
| 2004/0138555 A1 | 7/2004 | Krag et al. |
| 2006/0283007 A1 | 12/2006 | Cros et al. |
| 2007/0236213 A1 | 10/2007 | Paden et al. |
| 2008/0001756 A1 | 1/2008 | Dimmer et al. |
| 2009/0209852 A1 | 8/2009 | Mate et al. |
| 2009/0326560 A1* | 12/2009 | Lampropoulos .. A61M 25/0108 604/529 |
| 2010/0276501 A1 | 11/2010 | Yoshimura et al. |
| 2015/0126829 A1 | 5/2015 | Bernstein |
| 2016/0261233 A1 | 9/2016 | Pohl et al. |
| 2017/0234741 A1 | 8/2017 | Erickson et al. |
| 2019/0022412 A1 | 1/2019 | Vertatschitsch et al. |
| 2020/0060578 A1 | 2/2020 | Pooley et al. |

\* cited by examiner

TRACKING SYSTEM AND MARKER DEVICE TO BE TRACKED BY THE TRACKING SYSTEM

CROSS REFERENCE TO RELATED APPLICATIONS

This application claims priority to EP Application No. 19181514.1 filed Jun. 21, 2019 and is incorporated herein by reference.

FIELD OF THE INVENTION

The invention relates to a tracking system for a marker device attached to a medical device, a respective marker device, a corresponding medical device, a tracking method and tracking computer program for tracking the marker device.

BACKGROUND OF THE INVENTION

Invasive, and in particular minimally invasive, medical procedures are a commonly used tool to correctly assess and/or treat intravascular conditions in a patient.

It is known to track a medical device used for such procedures electromagnetically, especially in minimally invasive medical procedures. However, such electromagnetic tracking has the disadvantage that, for determining not only the position, but also the orientation of the medical device, the medical device needs to be equipped with several electromagnetic marker devices, wherein each marker device is adapted for, for instance, a three degrees of freedom (DoF) or five degrees of freedom (DoF) localization.

Moreover, typically known electromagnetic marker devices are significantly larger than 1 mm. For instance, the electromagnetic marker device used by the tracking system disclosed in the article "Validation of the Calypso Surface Beacon Transponder" by B. Maxwell et al., Journal of Applied Clinical Medical Physics, volume 17, pages 223-234 (2016) has a size of 8 mm.

As a further issue, electromagnetic marker devices often cannot be read out from a relatively large distance being, for instance, larger than 30 cm. For example, the system disclosed in the above mentioned article by B. Maxwell et al. allows reading out the marker devices from a distance of about 16 cm.

SUMMARY OF THE INVENTION

It is therefore an object of the present invention to provide an improved tracking system and an improved marker device, a respective medical device, a tracking method and a computer program for tracking the marker device. More particularly, it is an object of the present invention to provide a marker device that is small in size and capable of accurately indicating the position of a medical device for being used during surgery of a human being, in particular a patient on whom a minimally invasive procedure is performed. It is a further object of the invention to provide a tracking system capable of accurately tracking such a marker device.

According to a first aspect of the invention, a tracking system for tracking a marker device is provided, the marker device being attached to a medical device and the tracking system being for use in surgery. The marker device comprises a sensing unit comprising a magnetic object providing a permanent magnetic moment, wherein the sensing unit is configured to transduce an external magnetic or electromagnetic excitation field into a mechanical oscillation of the magnetic object. The tracking system comprises a field generator for generating a predetermined magnetic or electromagnetic excitation field for inducing mechanical oscillations of the magnetic object of the sensing unit, a transducer for transducing a magnetic or electromagnetic field generated by the induced mechanical oscillations of the magnetic object into one or more electrical response signals, and a position determination unit for determining the position of the marker device on the basis of the one or more electrical response signals.

Accordingly, a tracking system is provided that may be used to track the position and/or orientation of a medical device using a respective marker device attached to the medical device. This tracking system may particularly be employed to track the position and/or orientation of the medical device during surgery, even more particularly during minimally invasive surgery, such as to allow an accurate position and/orientation determination for the medical device using a marker device of a rather small size.

For this purpose, the tracking system uses a marker device comprising a sensing unit with a magnetic object having a permanent magnetic moment. If the sensing unit of the marker device is then subjected to a predetermined external magnetic or electromagnetic excitation field, the magnetic object starts oscillating in response to the excitation field. The mechanical oscillations of the magnetic object generate a magnetic or electromagnetic (response) field which is then transduced, by a respective transducer, into one or more electrical response signals. These response signals are then used to derive the position of the marker device. More particularly, the mechanical oscillations of the magnetic object may typically generate a position-dependent magnetic field variation which can be expressed in terms of the response signals and used, by the position determination unit, to determine the position of the marker device and, hence, the medical device to which the marker device is attached.

In this context, the term medical device may particularly refer to a device that is used for a medical procedure. In some embodiments, the medical device may particularly correspond to a device used during surgery, in particular minimally invasive surgery. In some embodiments, a medical device may refer to an interventional tool that is used for interventional procedures performed on a human being, in particular a patient.

In general, the position determination approach using a tracking system and a marker device as suggested herein may be used for any medical device for which it is beneficial to perform position determination/localization. As such, in some embodiments, the term medical device may also be used to any further medical device for which localization may be useful. As an example, a bandage or a patch shall be mentioned. For these cases, it may be important to track the position and/or orientation of these kinds of bandages or patches for safety reasons, e.g. after a surgery, in order to ensure that everything has been appropriately placed or removed (where needed).

The term marker device may particularly be used to refer to any device capable of indicating the position and/or orientation of an object the marker device is attached to. Specifically, the term marker device may refer to a device comprising a magnetosensitive sensing unit, i.e. a sensing unit including a magnetic object which responds to a magnetic or electromagnetic excitation field by performing respective mechanical oscillations, in particular rotational oscillations. These mechanical oscillations are used by the tracking system to generate the electrical response signals that are used for deriving the position (and orientation) of the marker device.

The term field generator may particularly refer to a generator of a magnetic or electromagnetic excitation field. In some embodiments, the field generator may comprise a magnetic field generation array including a plurality of generation units. In some embodiments, these generation units may particularly correspond to respective coils which are arranged in a coil array. In some embodiments, each one of the coils may be independently controlled. In some embodiments, such independent control may be used to provide a non-uniform magnetic or electromagnetic excitation field, ideally having a constant field gradient over the work space of the field.

In general, the present concept is based on the fact that the response by the magnetic object to a magnetic or electromagnetic excitation field (measured in terms of a mechanical oscillation) may provide an information on the position and/or orientation of the marker device comprising the sensing unit including the magnetic object. This is the case since the magnetic or electromagnetic excitation field may influence the magnetic object differently depending on the relative position between the magnetic object and the magnetic or electromagnetic excitation field.

Different possible approaches may be used to determine the position, i.e. to perform localization, of the marker device and, thereby, the medical device the marker device is attached to, based on the response of the mechanical oscillator to the magnetic or electromagnetic excitation field. In this context, two particular position determining approaches, also termed localization approaches, may be used. One approach would be performing the position determination based on coil sensitivity of different coils in the coil array. This approach is based on the fact that each coil in a coil array of a field generator has a different spatial sensitivity profile $B_{S,i}(r)$ based on its position and orientation in the tracking system. In that case, the magnetic object of the sensing unit will react with a characteristic mechanical oscillation for each coil, in particular with a characteristic amplitude which is determined by the dynamic dipole moment $$\frac{d}{dt}m(t)$$

for the mechanical object relative to $B_{S,i}(r)$.

The other approach would be based on gradient field encoding. This approach makes use of the fact that the frequencies of the marker devices can be manipulated to give an independent position information. For this purpose, a non-uniform magnetic field, ideally having a constant field gradient over the work space, may be generated, e.g. by applying low frequency currents to selected ones of the coils in the coil array. Such a non-uniform field could for example be achieved by providing the above-mentioned independent control of the coils.

This additional field changes a restoring field $B_{rest}$ acting on the magnetic object of the sensing unit and, thus, changes the frequency of the oscillation. Due to the non-uniform nature of the magnetic or electromagnetic field, this frequency change will depend on the position and orientation of the marker device.

The specifics of these localization approaches will further be discussed herein below. In some embodiments, one such approach may be sufficient, while in other embodiments, a combination of both approaches may be useful to increase accuracy or to identify systematic errors (e.g. a strong ferromagnet in the workspace) that might lead to contradicting results between the two methods.

In some embodiments, the position determination unit may be adapted to determine, on the basis of the or more electrical response signals, at least five degrees of freedom for the marker device relative to a coordinate system provided by the tracking system, the at least five degrees of freedom including a position and at least two orientation angles of the marker device relative to the tracking device.

In some embodiments, the tracking system may define or be provided with a coordinate system and the marker device may be localized relative to said coordinate system. For this purpose, the position determination unit may be adapted to determine, based on the one or more response signals, at least five degrees of freedom (DoF) for the marker device. These five degrees of freedom may allow to determine the position as well as the orientation (in terms of two orientation angles) of the marker device relative to the coordinate system of the tracking system. Hence, by means of this arrangement, it becomes possible to determine the position and the orientation of a marker device and, accordingly, a medical device to which the marker device is attached, using only one marker device.

According to some embodiments, the tracking system may be adapted to determine the position of a plurality of marker devices, each of the plurality of marker devices comprising a respective sensing unit. The magnetic objects of the respective sensing unit may be oscillatable, in particular rotationally oscillatable, with different resonance frequencies such as to generate a different magnetic or electromagnetic field to be transduced in respective one or more electrical response signals specific to the respective marker device. The position determination unit may then be provided for determining the position of one or more of the plurality of marker devices based on the respective one or more electrical response signals.

Preferentially the tracking system is adapted to determine the position of several marker devices, wherein the magnetic objects of the several marker devices are oscillatable, preferably rotationally oscillatable, with different resonant frequencies such that the induction signals of different marker devices have different frequencies, wherein the position determination unit is adapted to determine the positions of the marker devices based on the generated induction signals having the different frequencies. The position determination unit is preferentially also adapted to determine the orientation of the marker devices based on the generated induction signals having the different frequencies. By using the different marker devices with different resonant frequencies, it is possible to distinguish between different marker devices and to determine, for each marker device, the respective position and preferentially also the respective orientation.

The several marker devices can be attached to a single medical device, wherein the position determination unit can be adapted to determine the shape and/or position and/or orientation of the medical device based on the determined positions of the several marker devices. Further, the position determination unit may be adapted to determine the shape and/or position and/or orientation of the medical device based on orientations determined for the several marker devices. While the marker devices may particularly be used to determine a shape and/or position and/or orientation of a medical device, it shall be understood that the marker devices may also be used to determine the shape and/or position and/or orientation of other elements onto which the plurality of marker devices is attached, such as e.g. body tissue or the like. In some embodiments, the plurality of marker devices may also be distributed amongst a medical device used for treatment of tissue and the respective tissue to gather information about both elements and/or the relationship of both elements to one another.

In an embodiment the position determination unit is adapted to determine the position of one particular marker device relative to a position of another marker device. Also, the orientation of the marker device can be determined relative to the orientation of another marker device. However, the position and optionally also the orientation can also be determined relative to another reference. To that end, the tracking system may also be provided with a respective output unit for outputting the determined position and/or orientation of the marker device.

In some embodiments, the tracking system position determination unit may be configured to compensate a dependence of the one or more electrical signals on a temperature. In some embodiments, the position determination unit may be configured to apply a compensation algorithm, in order to perform such compensation.

In a preferred embodiment the tracking system, and in particular the position determination unit, may be configured to compensate a dependence of the one or more electrical signals on the temperature. For that purpose, the temperature-dependent behavior of the magnetic object, i.e. the temperature-dependence of its resonance frequencies is preferably determined, either experimentally or by respective calculations.

In some embodiments, the tracking system may then be provided with a temperature sensor and/or an input means for inputting the temperature. An algorithm may then be provided which takes into account the input temperature and correlates it with the known dependency of the resonance frequency of the magnetic object in order to compensate for the temperature-dependence. This allows to remove the temperature effects from the electrical signals, thereby resulting in a more accurate position determination/localization approach. That is, in some embodiments, the temperature compensation may be performed by means of a compensation algorithm, i.e. is implemented in program code.

Alternatively or additionally, it may also be possible to obtain temperature compensation by different means such as a physical compensation element. That is, in some embodiments, the marker device itself, and, more particularly, the sensing unit may be capable of compensating a dependence of the resonance frequency of the mechanical oscillation of the magnetic object on the temperature. For that purpose, the sensing unit may comprise a compensation element which is adapted to modify the resonance frequency in a first frequency direction depending on a temperature change which is opposite to a second frequency direction in which the resonance frequency of the sensing unit would be modified depending on the temperature change if the compensation element were not part of the sensing unit. This arrangement allows to reduce or even eliminate temperature induced shifts of the resonance frequency. Hereby, the first frequency direction may particularly correspond to a direction towards higher or lower frequencies and the opposite second frequency direction may correspond to a direction towards lower or higher frequencies, respectively.

Preferentially the compensation element comprises magnetic material which changes its magnetization and thereby the resonant frequency with temperature, wherein the magnetic material is chosen and arranged within the sensing unit, particularly within a casing of the sensing unit, such that the direction of the modification of the resonance frequency is the first frequency direction. The compensating magnetic material is preferentially arranged adjacent to the magnetic object and/or adjacent to a further magnetic object as described herein below. This allows to design the marker device such that an unwanted temperature dependence can be significantly reduced or even eliminated in a technically relatively simple way and without requiring much space within the casing.

In some embodiments, the position determination unit may be configured to apply a compensation algorithm in order to compensate for one or more of: static background fields, and dynamic background fields.

In some embodiments, the position determination unit may further apply a compensation algorithm to compensate for static and/or dynamic background fields. Static background fields add to the field of the fixed magnetic object and thus modulate the restoring field $B_{rest}$ seen by the oscillating magnetic object. Accordingly, the resulting resonance frequency is changed, which may be a source of error for performing position determination using the oscillating magnetic object's frequency changes.

In some embodiments, the compensation may be performed by a respective algorithm implemented in the tracking system, and particularly applied by the position determination unit. For that purpose, the tracking system may be provided with one or more absolute field sensors adapted to measure magnitude and orientation of static background fields. Based on the orientation of the marker device, a frequency or field correction can be calculated to arrive at the correct position and/or orientation value.

For sensing static background fields, any magnetic field sensor with sufficient sensitivity and a footprint that can be integrated in the tracking system may be used. As an example, a 3-axis Hall sensor shall be mentioned. Alternatively or additionally, a 3-axis array of temperature-compensated micro-bots with a well-defined zero-field frequency may be used. From the change to their respective frequencies, the magnitude and orientation of the background fields can be determined. Ideally, their resonance frequencies are chosen such that they do not interfere with the frequency of the sensing unit.

Instead of correcting for the frequency offset in the evaluation, one can also use the coils of a multi-coil tracking systems to generate small offset fields to counter-balance background fields and/or even the earth-magnetic fields. If inhomogeneous fields exist in the field of view due to the presence of ferromagnetic material, several sets of 3-axis magnetic field sensors can be employed to characterize the spatial field variations. Based on an interpolated background field map derived from these measurements, a correction for the sensing unit at known position and orientation can be calculated or the respective correcting offset fields can be applied or a mixture of the two correction methods is used.

According to some embodiments, it is also possible to mitigate the static and/or dynamic background field effect on the marker device side. In this case, the sensing unit of the marker device can be designed such as to employ two suspended spheres having an identical magnetic dipole moment and moment of inertia (or a suitable ratio of the two quantities). Since the counter-oscillation occurs at a single frequency, the first order effect of a static bias field like the earth magnetic field is cancelled.

In some embodiments, the position determination unit may be configured to apply a compensation algorithm in order to compensate for non-linearity resulting from different oscillation amplitudes of the mechanical oscillations.

The position determination unit may be configured to compensate for non-linearity in the system that may result from different oscillation amplitudes of the mechanical oscillations of the magnetic object of the sensing unit. In some embodiments, this may particularly encompass a further optional data processing step in which an inverse non-linear filter is applied to reduce the non-linearity of the tracking system. Hereby, the non-linearity of the tracking system is measured and a computational filter is constructed to reverse the effect of the non-linearity. This is especially useful if low cost components are used because they tend to have more non-linear behavior.

Alternatively, the non-linear filter may be used as a first processing step. If more than one signal is used, there are further signal processing steps. If at least one receive channel is not detecting a response from the sensing unit of the marker device and thus provides a measure of the background signal, this (and all other such signals) are correlated with the received signal and the correlating components are subtracted from the signal bearing channels. This subtraction can be done in time or frequency domain or a mixture of both. If there are no channels without any sensor signal, a data processing strategy sometimes called "virtual gradiometer" may be used. This decomposes the multitude of channels in virtual channels that are linear combinations of the physical channels to minimize interference of response signals not generated by the sensing. The factors for the linear combinations may be found by correlating the signals of the channels excluding the signal band of the sensing unit or sensing units.

In some embodiments, the field generator may comprise a magnetic field generation array comprising a plurality of generation units arranged in a predetermined spatial arrangement. Here, the one or more electrical response signals may be indicative of a characteristic mechanical oscillation of the magnetic object of the sensing unit induced by each of the plurality of generation units, wherein the position determination unit is adapted to determine the position of the marker device at least partially based on the one or more electrical response signals being indicative of the characteristic mechanical oscillation. In some embodiments, the position determination unit is adapted to determine, from the one or more electrical response signals, an amplitude of the characteristic mechanical oscillations of the magnetic object for each one of the plurality of generation units.

In some embodiments, the field generator may comprise a plurality of generation units spatially arranged in a magnetic field generation array. In some embodiments, this spatial arrangement may be two-dimensional. However, also three-dimensional spatial arrangements may be envisioned. In some embodiments, the magnetic field generation array may correspond to a coil array and the generation units may correspond to one or more coils. In such a case, the position estimation/localization may be performed at least partially based on coil sensitivity of the individual coils in the coil array. This approach will be described in detail further below.

In some embodiments, the tracking system may further comprise a control unit, and the field generator comprises a or the magnetic field generation array comprising a plurality of generation units arranged in a predetermined spatial arrangement, wherein each one of the plurality of generation units is adapted to be controlled independently of the remaining ones of the plurality of generation units by the control unit, the control unit being adapted to control at least some of the generation units such that at least one spatial excitation field component of the magnetic or electromagnetic excitation field is modifiable by said control, wherein the position determination unit is adapted to determine the position of the marker device at least partially based on the one or more electrical response signals being indicative of the modifying of the at least one spatial excitation field component. In some embodiments, the field generator is adapted to sequentially generate a set of different additional magnetic or electromagnetic encoding field varying in space and/or time, wherein the position determination unit is adapted to determine the position of the marker device at least partially based on the one or more electrical response signals transduced by the transducer based on a magnetic or electromagnetic field generated by the induced mechanical oscillations of the magnetic object in response to each of the set of different additional magnetic or electromagnetic encoding fields.

The localization can also be carried out based on gradient field encoding. While the coil-sensitivity localization is based on the amplitude distribution picked up by the coil array, the frequencies of the markers can be manipulated to give an independent position information. To this end, a non-uniform magnetic field, ideally having a constant field gradient over the work space, is generated, e.g. by applying low frequency currents to selected coils of the coil array.

This additional field changes the restoring field $B_{rest}$ acting on the oscillation magnetic object and thus its frequency. Due to the non-uniform nature of the field, the frequency change will depend on position and orientation of the marker. By sequential application of several encoding fields (e.g. a field gradient applied in 6 different orientations), all three position and two of three orientation parameters of a marker can be determined. The remaining angle can be deferred from the higher order response of the sensor to external magnetic fields, however, at the cost of higher field strengths needed for generating sufficient higher order contributions. The basic encoding idea is related to gradient encoding in MRI; thus, both frequency encoding and phase encoding can be done.

For frequency encoding, the non-uniform field is applied during signal readout to produce the desired frequency offset. For a desired spatial resolution, the applied encoding field strength must be adapted to the frequency sensitivity of the marker devive and the frequency resolution the tracking system delivers.

For phase encoding, the non-uniform encoding field is applied prior to the signal readout, i.e. the position-dependent frequency offset is only applied for a short window during which a position-dependent signal phase offset accrues. In case that the phase resolution is not sufficient for accurate position determination/localization, the duration and/or amplitude of the phase encoding pulses can be varied in sequential excitations, so that ambiguities in phase accruals (larger than 2 pi) can be discerned. Thus, full spatial information is obtained over the course of several readouts.

Phase encoding with one non-uniform field pattern (e.g. encoding one spatial axis) can be combined with frequency encoding with another non-uniform field pattern (e.g. encoding an orthogonal spatial axis) for efficient localization. If a rough marker position is already known from the sensitivity-encoding approach (which is faster due to its parallel nature), it will suffice to only use few phase-encoding steps that provide the missing high resolution (high spatial frequency) components, but not the complete spatial information.

As described in this description, comparison of localization results obtained with gradient versus sensitivity encoding can be used to identify systematic errors, e.g. resulting from background fields. Furthermore, it should be noted that the linear response to low-frequency external fields of sensing units employing e.g. two suspended magnetic spheres as the magnetic objects may be suppressed; in that case the higher order response of the frequency can be used not only for localization, but also for sanity checks. However, the field sensitivity of these oscillators is much lower so that higher gradient fields will be needed for gradient field encoding.

In another aspect, a marker device for being attached to a medical device is provided. The marker device comprises a casing and a sensing unit comprising a magnetic object providing a permanent magnetic moment. The sensing unit is configured to transduce an external magnetic or electromagnetic excitation field into a mechanical oscillation of the magnetic object, wherein the induced mechanical oscillation is independent of an external pressure the sensing unit is subjected to. In some embodiments, the casing may particularly be a hard casing. In some embodiments, the marker device may have an elongated shape with a maximum dimension being smaller than or equal to 5 mm and a minimum dimension being smaller than or equal to 1 mm. In some embodiments, the magnetic object may be arranged within the casing such as to be rotatable out of an equilibrium orientation if the external magnetic or electromagnetic excitation field is acting on the magnetic object. Hereby, the sensing unit may further comprise a restoring torque unit for providing a restoring torque to return the magnetic object back into the equilibrium orientation if the external magnetic or electromagnetic excitation field has rotated the magnetic object out of the equilibrium orientation such as to allow the mechanical oscillation of the magnetic object with a resonance frequency.

According to a further aspect, a marker device is provided which allows to determine the position and/or orientation of a medical device to which the marker device may be attached. The marker device may comprise a casing and a sensing unit. The sensing unit allows to transduce the external magnetic or electromagnetic excitation field generated by the field generator into a mechanical, preferably rotational, oscillation of a magnetic object which is provided in the sensing unit and has a permanent magnetic moment.

The sensing unit comprising the magnetic object may particularly comprise or be provided inside the casing. Specifically, the magnetic object may be arranged within the casing. Hereby, the magnetic object may particularly be arranged within the casing such that it may be rotatable out of an equilibrium orientation by an external magnetic torque acting on the magnetic object. The external magnetic torque may be a result of the external magnetic or electromagnetic field acting on the magnetic object. That is, in some embodiments, the magnetic object is rotated out of its equilibrium position by the external magnetic or electromagnetic field.

The sensing unit may further comprise a restoring torque unit for providing a restoring torque to force the magnetic object back to the equilibrium orientation if the external magnetic or electromagnetic field has rotated the magnetic object out of the equilibrium orientation. This results in a rotational oscillation of the magnetic object excited by the external magnetic torque from the external magnetic or electromagnetic field. The rotational oscillations are hereby performed, by the magnetic object, with a respective resonance frequency that is dependent on the spatial position and orientation of the sensing unit, and, hence, the marker device, in the external magnetic or electromagnetic field. The resulting magnetic or electromagnetic field generated by the mechanical, rotational oscillations of the magnetic object may then be transduced into respective one or more response signals. These response signals are hereby dependent on the resonance frequency of the oscillations.

In some embodiments, the rotational oscillations may particularly ultimately result in respective induction signals, whereby these induction signals depend on the spatial position and orientation of the marker device in the external magnetic or electromagnetic field. These induction signals may particularly be generated in an excitation and induction signal unit of a tracking system. In particular, the excitation and induction signal unit can comprise i) first coils adapted to generate the magnetic field providing the magnetic torque for rotating the magnetic object of the tracking device out of its equilibrium orientation and to thereby excite the rotational oscillation of the magnetic object and ii) second coils adapted to generate the induction signals that depend on the spatial position and orientation of the marker device. This allows determining the position and orientation, i.e. six degrees of freedom, of the marker device such that it is possible to determine the position and the orientation of a medical device equipped with this marker device by using only a single marker device.

Additionally, this arrangement allows for the tracking system to perform tracking based on the marker device from a relatively large distance which is, for instance, larger than 30 cm. Furthermore, the marker device can be relatively small, for instance, smaller than 1 mm. To that end, in some embodiments, the casing of the marker device may be cylindrical and the outer diameter of the cylinder is smaller than 1 mm, further preferred smaller than 0.5 mm and even further preferred smaller than 0.3 mm.

Preferentially, the magnetic object is rotatable around a virtual rotational axis centrally traversing the magnetic object, wherein the magnetic object is rotationally symmetric with respect to the virtual rotational axis. In particular, the magnetic object may be a magnetic sphere or a magnetic cylinder. Moreover, the restoring torque unit may comprise a torsional spring mechanism for providing the restoring torque. In addition or alternatively, the restoring torque unit might also comprise a further magnetic object for providing the restoring torque.

In an embodiment the magnetic object is attached to one end of an attachment portion, such as a filament, wherein another end of the attachment portion is attached to the casing. The attachment portion may be adapted to prevent that the magnetic object touches the further magnetic object embodying the restoring torque unit due to their magnetic attraction and to allow the magnetic object to rotationally oscillate. The further magnetic object is preferentially stationarily respectively fixedly attached to the casing. However, the further magnetic object can also be arranged within the casing such that it is rotationally oscillatable relative to the casing. In particular, the further magnetic object can also be attached to one end of another attachment portion, such as a filament, wherein another end of the attachment portion can be attached to the casing.

In a preferred embodiment the further magnetic object is rotatable around a virtual rotational axis centrally traversing the further magnetic object, wherein the further magnetic object is rotationally symmetric with respect to the virtual rotational axis. Also the further magnetic object might be a magnetic sphere or a magnetic cylinder. Moreover, the virtual axes of the magnetic object and the further magnetic object are preferentially aligned with each other.

These techniques allow to provide a restoring torque and hence a rotational oscillation of the magnetic object such that the overall marker device can be relatively small, the resonant frequency of the marker device can be provided as desired and the construction of the marker device can still be relatively simple.

Now, in order to perform position determination, the resulting mechanical rotational oscillation of the magnetic object has to be independent of any external pressure the sensing unit is subjected to. As an example, if the marker device is used for tracking of a medical device that is used in an invasive procedure, the oscillation of the magnetic object inside the marker device should not be influenced by any pressure acting on the medical instrument from the outside, such as blood pressure or circulatory pressure or the like.

For that purpose, the marker device is provided with a casing in which the sensing unit is situated, whereby this casing may have one or more hard walls and may particularly be a hard casing, i.e. a casing having walls that do not change their shape in case of external pressure acting thereupon. This means, that the positioning of the magnetic object inside the casing remains largely unaffected by outside pressure due to the walls not bending in response to the outside pressure. This, in turn, results in the distance between the magnetic object and the restoring torque unit, which is also provided in the casing, remaining the same, independent of the pressure acting from the outside on the sensing unit. Accordingly, the magnetic forces acting between the magnetic object and the restoring torque unit do not change due to distance changes caused by a pressure-induced bending of any walls of the cases and, as such, are independent of any external pressure acting on the sensing unit. Accordingly, the resonance frequency of the rotational oscillation caused by the external magnetic or electromagnetic field acting on the magnetic object is not affected by any distance changes either. This means that any resonance frequency changes are mostly influenced by the position and orientation of the sensing unit, and, hence, the marker device, in the external magnetic or electromagnetic field. As a result, the sensing unit may be employed for position determination/localization of the marker device and, as such, any medical device the marker device is attached to.

By means of such a magnetic object situated in a (hard) casing, a small marker device may be provided which may have rather small size of even below 1 mm. This makes the marker device particularly suitable for being used in a tracking system for tracking a medical device during minimally invasive surgery.

According to yet another aspect, a medical device for use during surgery is provided, the medical device having a marker device as previously described attached thereto. The marker device is to be tracked by a tracking system as previously described. In some embodiments, the medical device comprises a tip adapted such as to have the marker device attached thereto. In some embodiments, the medical device may comprise one or more of an interventional device or an implant, in particular an electrical implant and/or an orthopedic implant. In some embodiments, the medical device may particularly comprise one or more of: a surgical instrument, an imaging probe, an endoscope, a bronchoscope or an ingestible pill. Alternatively or additionally, the medical device may comprise one or more of a catheter, a wire, in particular a guidewire, a stent, one or more aneurism coilings, one or more vena cava filters, a heart valve, a shunt, a needle, a wire, a tube, a stylet or a radioactive seed. In some embodiments, the medical device may have a longitudinal shape. The medical device may be adapted to have a plurality of marker devices as described herein above attached thereto, wherein the plurality of marker devices may be arranged along longitudinal axis of said medical device.

According to another aspect, a tracking method for tracking a marker device as previously described is provided, the marker device being attached to a medical device as described herein above using a tracking system as described. The tracking system may particularly be used during surgery. The tracking method comprises generating a magnetic or electromagnetic excitation field for inducing mechanical oscillations of the magnetic object of the sensing unit, transducing a magnetic or electromagnetic field generated by the induced mechanical oscillations of the magnetic object of the sensing unit into one or more electrical response signals, determining a position of the marker device on the basis of the one or more electrical response signals. In yet another aspect, a computer program comprising program code means for causing a tracking system as previously specified to carry out the steps of the above-mentioned tracking method, when the computer program is run on a computer controlling the tracking system.

DETAILED DESCRIPTION OF EMBODIMENTS

Figure 1:
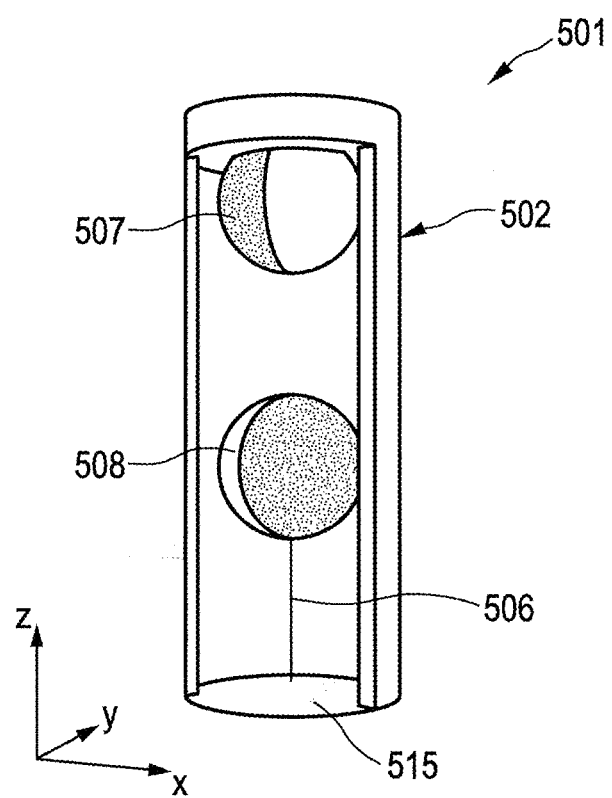
FIG. 1 shows schematically and exemplarily an embodiment of a marker device according to a first embodiment.

FIG. 1 schematically and exemplarily shows an embodiment of a marker device 501 for being attached to a medical device for being tracked by a tracking system used during surgery, in particular minimally invasive surgery on a human being, in particular a patient. The marker device 501 comprises a sensing unit with two magnetic object 507, 508.

The magnetic object 508 is suspended from an attachment portion 506, such as a filament, and is thus free to perform a rotational motion about the main axis of the sensing unit. In this embodiment, the further magnetic object 507 is fixed. However, in another embodiment the further magnetic element can also be suspended from an attachment portion, such as a filament, and thus can be free to perform a rotational motion about the main axis of the sensing unit.

In equilibrium, the magnetic objects 507, 508, respectively, align with anti-parallel orientation of their magnetization. An external magnetic field pulse can be used to start a resonance rotational oscillation. The attractive force determines the resonance frequency of the oscillation, which for a spherical suspended magnet is given by $$\omega_0 = \sqrt{\frac{5M_S B}{2\rho r^2}}, \tag{1}$$

where $M_S$ is the saturation magnetization of the magnetic material, $\mu$ is its density, r is the sphere diameter, and B is the field created by the fixed magnetic object. It can be approximated as a dipole field $$B(r) = \frac{\mu_0}{4\pi}\left(\frac{3r(m \cdot r)}{r^5} - \frac{m}{r^3}\right), \tag{2}$$

where m is the magnetic moment of the magnetic object.

The field variation generated by the oscillating magnetic object 508 can be detected via the induced voltage in one or several detection coils of a transducer, which is configured to transduce a magnetic or electromagnetic field generated by the mechanical oscillations of the magnetic object 508 of the sensing unit into electrical response signals. The time trace of the detected signal can be Fourier-transformed to obtain the spectrum, which enables determination of the resonance frequency.

Due to the low resonance frequencies of a few kHz, the magnetic fields are not shielded by metal and thus all non-ferromagnetic metals can be used as structural or coating materials. Likewise, the marker device can be placed into non-ferromagnetic metallic objects without effects on its operation, as long as the metal thickness does not strongly exceed the skin depth. At these frequencies, for very good conductors like copper, the skin depth is of the order of one millimeter, while for Nitinol, the skin depth is around 10 millimeters.

The sensing unit 501 thus contains two magnetic objects 507, 508, wherein, in equilibrium, the magnetic objects 507, 508 align with anti-parallel magnetization. An external field pulse provided by a respective field generator can be used to start a rotational oscillation of the suspended magnetic object 508—which, in the embodiment of FIG. 1 corresponds to a magnetic sphere—about the main axis of the sensing unit, wherein the other magnetic object 507—also embodiment as a magnetic sphere in this particular embodiment—is fixed. If in another embodiment also the other magnetic object 507 is suspended in free space and can perform a rotational oscillation, both magnetic objects 507, 508 can perform a resonance counter-oscillation.

The use of magneto-mechanical oscillators to determine a position and/or orientation of a marker device relative to a tracking system is known. Further, the use of LC oscillators for performing such a position estimation is known. A marker device including a sensing unit is e.g. shown in the article "Validation of the Calypso Surface Beacon Transponder" by B. Maxwell et al., Journal of Applied Clinical Medical Physics, volume 17, pages 223-234 (2016). However, the marker devices shown therein typically have a size of 8 mm. It would be beneficial to provide marker devices of a smaller size. Unfortunately, with decreasing size of the marker device, the accuracy of the measurement also decreases. Accordingly, position determination measurements using the above-cited marker devices is not ideal, in particular for small-size marker devices.

That is, with reduced size, the power level that can be generated at the oscillator and the dynamic dipole moment generated by the power diminish. This can be seen in the following equation. The quality factor of the resonator cannot be higher than the quality factor of the coil. An approximation for the quality factor of the coil can be written as:

$$Q = \omega \frac{\mu_0}{2\rho} \tau r^2, \tag{3}$$

where $\omega$ is the frequency, $\mu_o$ the vacuum permeability, p the resistivity, r the fraction of the radius consisting of conductor, and r the radius of the coil. The coil is assumed to be cylindrical with diameter matching the height. For a 1 mm diameter copper coil at 100 kHz, a quality factor of about 1 is achieved. Thus, typically, the maximum possible quality factor achievable in mechanical resonances is too low for efficient operation. There are some materials like fused silica that would offer a high quality factor in the oscillation. These materials are usually quite hard and do not allow for a high enough oscillation amplitude (high enough angle) to be efficient, i.e. to generate a sufficiently large field variation. This may lead to a need for a quite high signal to noise ratio which in turn results in the need for a high amount of magnetic material which makes the sensor large.

The above formula overestimates the practically achievable Q values as it assumes that all volume is filled with conduction material and neglect proximity and skin effects as well as the losses in the capacitor. Nonetheless, these values lead to a working system. As the dynamic dipole moment of e.g. an LC oscillator is Q times external magnetic field times volume, the signal scales with $r^5$, while in the case of a mechanical oscillator (energy stored in elasticity) the signal scales with $r^3$, and in the case of the embodiments described, for instance, with reference to FIG. 1 (magneto-mechanical oscillator, energy stored in magnetic field), the signal scales with $r^2$, as the frequency is inversely proportional to the linear dimensions. So the proposal presented here is very good suited for sensor miniaturization.

Accordingly, the above discussed problems are avoided by the design proposed, for instance, in FIG. 1. As the energy is stored mainly in the magnetic field, it is relatively easy to attain a high quality factor. High oscillation amplitudes are also easily possible. Usually, the sensing units may also employ an attachment portion, such as a thin filament, which is not subjected to strong wear. The resonance may thus be easily changed by changing the magnetic field by a mechanical movement of magnets relative to each other. This change may then be used to determine the position of the sensing unit relative to a coordinate system provided by the tracking system as further discussed below.

In the embodiment with a fixed sphere, the fixed sphere might have a diameter of 620 nm, whereas the oscillating sphere 108 might have a diameter of 500 nm. The magnetic moment of the oscillating sphere 108 might be $m \approx 70\ \mu Am^2$, the base frequency might be $f_0 \approx 2$ kHz, and the quality factor might be roughly $Q \approx 500$. SNR depends on distance between a) a coil used for reading out the resonance frequency and b) the sensing device as well as coil parameters. For a handheld coil with diameter 10 cm, 200 windings, and a resistance of 10 Ohm, the theoretically achievable SNR at a distance of about 30 cm and a sampling duration of 0.1 s is roughly 4000. However, typical SNR values of a demonstrator with a fixed sphere might be between 10 and 100, if hardly no measures for background signal suppression have been implemented. Noise is therefore mainly determined by fluctuations of the mains power supply harmonics. For half the sphere diameters, i.e., for instance, 250 μm for the oscillating sphere, magnetic moment could be $m \approx 9\ \mu Am^2$, the base frequency could be $f_0 \approx 4$ kHz, the quality factor could remain unchanged, and theoretical SNR could drop to about 1000.

There are several ways how to attach the attachment portion to the rotatable magnetic object 508.

For instance, a through hole attachment can be used. In this case a hole is drilled through the center of gravity and roughly perpendicular to the magnetization. Although the magnet material is hard and brittle, there are several methods to drill the holes, like pulsed laser or electrical discharge machining (EDM). The thread is run through the hole and glued in place. Running through is best done using a vacuum suction process. Several glue types can be used. Economic are light curing glues. They should have a low viscosity to fill the hole with the treads simply by capillary force. Additionally or alternatively, the attachment portion can be fixed to the magnetic object 508 by mechanical means, e.g. by having a knot in the thread or some other thick portion in the tread like a glue droplet or a heat generated (melted) bead. The latter is especially easily made in UHMWPE fibers. This attachment method reduces the magnetic dipole moment only by a small fraction and therefore retrains good signal. The shape of the magnetic object is not much altered which may be important in the case of spheres.

Also a clamp attachment can be used. In this case the magnetic object is split in at least two components. Preferably a split plane is generated orthogonal to the magnetization and parallel to the thread attachment direction. The thread, i.e. the filament, is placed on this plane. Precise alignment is not necessary. The second magnetic part is placed on top. The magnetic parts are usually held together by magnetic forces. Finally, glue is applied to secure everything in place. Preferred glue types are the same as in the through hole attachment process. In addition, it is possible to grind a groove in one or both of the magnetic objects to reduce the overall gap between the magnetic objects. This method produces results almost as good as the through hole method, but requires no special equipment for the manufacturing. Usually, the magnetic sub-objects are not made by splitting a single full magnetic object, but by grinding down two (identical) magnetic objects. The down side is that this process is more wasteful as two initial objects are used and it may be also somewhat more labor intense.

The cheapest method is the direct attachment of the thread top the magnetic object 508 using a suitable glue. The magnetic object 508 is held and aligned in some sort of tool. Both functions may be realized by suitable magnetic fields. The tool may be a funnel shaped with a thread running through the funnel and the magnetic object is attached to the funnel opening by magnetic forces. Glue is applied in the funnel and cured. Then the assembly is extracted from the tool and the unwanted portion of the tread is cut. This method can be very cheap and uses the magnetic object to full extend. The drawback is that considerable material is added, reducing oscillation frequency and requiring space in the completed device.

In a further embodiment, a structure to attach and additional gluing can be used. It is possible to attach the thread to the magnetic object 508 by first attaching it to a non-magnetic object and then gluing the non-magnetic object to the magnetic one. The non-magnetic object may be manufactured by injection molding or an equivalent cheap process. The shape of the non-magnetic object should allow for a simple thread attachment i.e. it may have a hole or a clamping mechanism, may be even as simple as a notch. The non-magnetic object is then glued to the magnetic object. Alternatively, it may be clamped or screwed to the magnetic object. This method is simple and cheap, but may need too much additional space for some applications.

In principle, all the methods discussed for thread-magnetic object attachment apply in the same way to thread-casing attachment. However, as the casing material is usually simpler to work with, the trough-hole method may be a good choice. Clamping is also a good option. This may be cheaper but may be harder to be finally sealed.

In the embodiment according to FIG. 1, at least the wall 515 of the casing 502 of the marker device is a hard wall, such as to be insensitive to external pressure. This avoids changes of the mechanical oscillation of the magnetic object 508 due to external pressure influences, as the distance between the magnetic object 508 and the restoring torque unit in terms of magnetic object 507 is maintained constant and, as such, the magnetic force interacting between these two magnetic objects is not changed due to (pressure-induced) inter-sphere distance changes. Accordingly, the resonance frequency is not affected by any inter-sphere distance changes either. This means that the mechanical oscillations of the magnetic object induced by the interaction of the external magnetic or electromagnetic excitation field and the restoring torque field of the magnetic object 507 are mostly dependent on the position and/or orientation of the marker device relative to the excitation field and, hence, allow a translation into the coordinate system provided by the tracking device.

Figure 2:
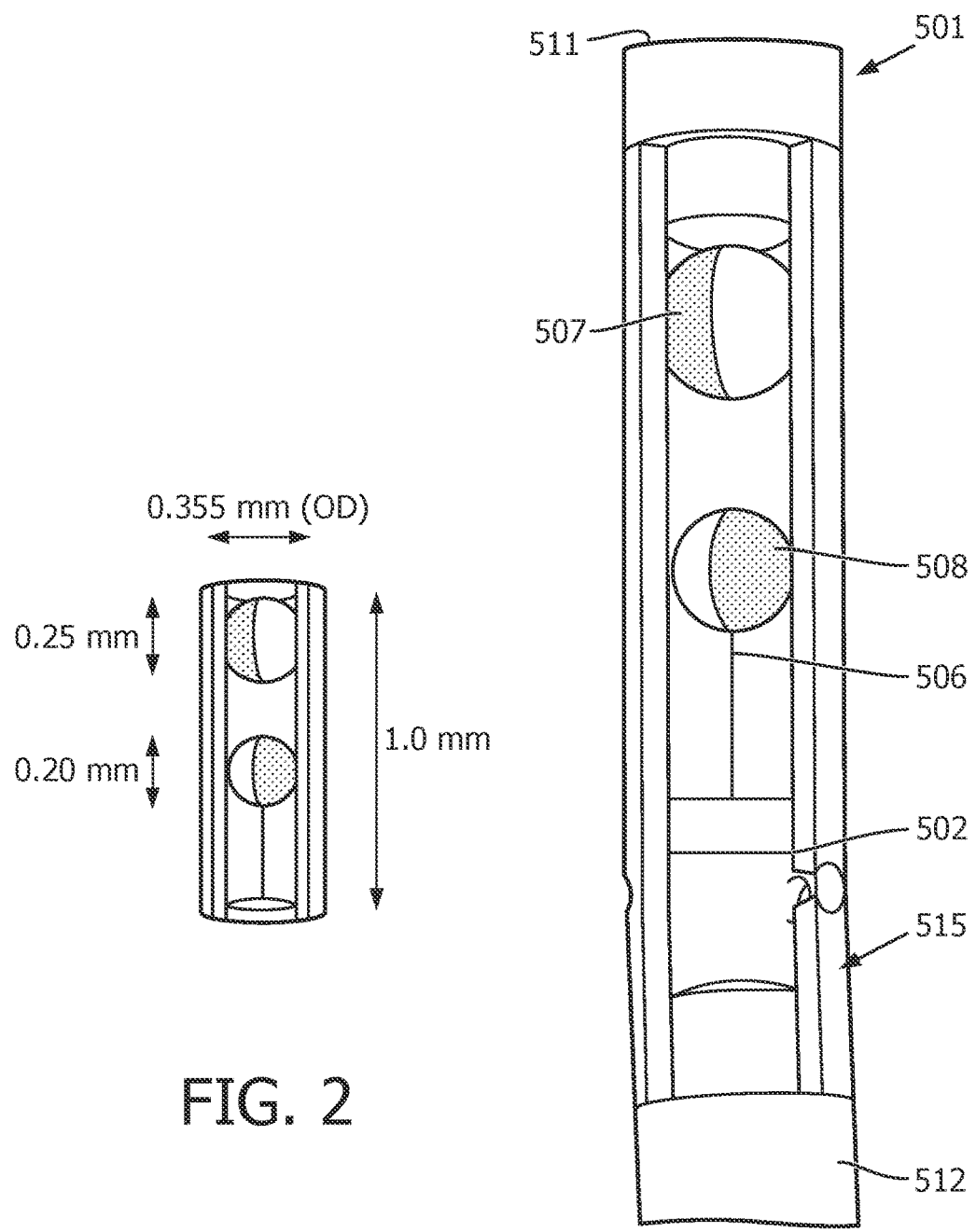
FIG. 2 shows schematically and exemplarily a marker device that is attached to a medical instrument.
Figure 3:
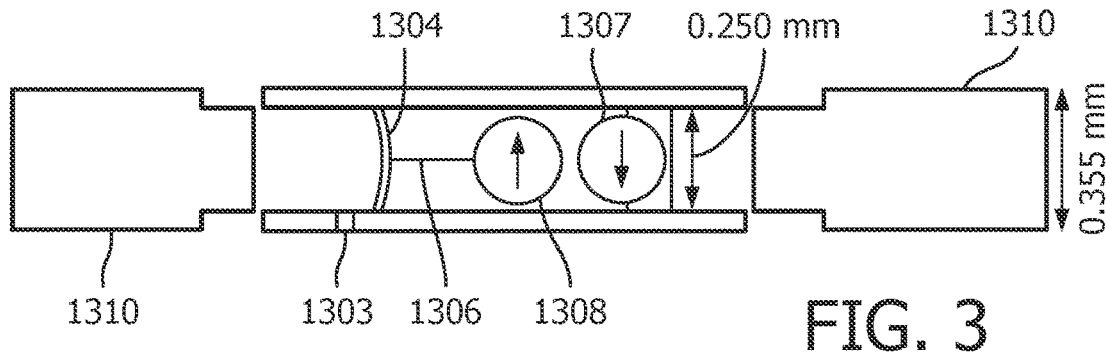
FIG. 3 shows a different perspective of the marker device and medical device according to FIG. 2.

The above-described marker device may be employed to be attached to any kind of medical device that should be tracked during a medical procedure. To that end, FIGS. 2 and 3 schematically illustrates a marker device 501 that is attached to a medical device 510. In the specific embodiment of FIGS. 2 and 3, the medical device 510 corresponds to a guidewire. It shall be understood, though, that the medical device can also be any other kind of medical device, in particular any other kind of medical instrument, even more particular any kind of medical instrument for performing (minimally invasive) surgery, for which tracking may be beneficial. In some embodiments, the marker device may also be used to track a different element, such as a tissue, a bandage, or the like. Examples for further devices and/or elements to be tracked are provided in FIGS. 4 to 6 and discussed further below.

As discussed, in the specific embodiment shown in FIGS. 2 and 3, the marker device 501 is attached to medical device 510, with medical device 510 corresponding to a guidewire. Portions 511 and 512 of guidewire 510 can be used to have a casing 502 of the marker device 501 with a fixed magnetic sphere 507 as the restoring torque unit and a rotatable magnetic sphere 508 attached to hard wall 515 via attachment portion 506 as the magnetic object attached to the guidewire.

The dimensions shown in FIGS. 2 and 3 are only exemplarily. The dimensions could also be different. However, the shown dimensions are very suitable for performing tracking during an interventional procedure on a human patient. Applying scaling laws to an observed demonstrator SNR shows that the indicated dimensions will give sufficient SNR and accuracy for remote operation at distances large enough to completely penetrate a patient. Thus, the marker device 501 can be attached to a guidewire, thereby allowing for tracking of the guidewire during the interventional procedure.

It may be useful to use the marker device also for other medical devices and/or other elements as shown in FIGS. 4 to 10.

Figure 4:
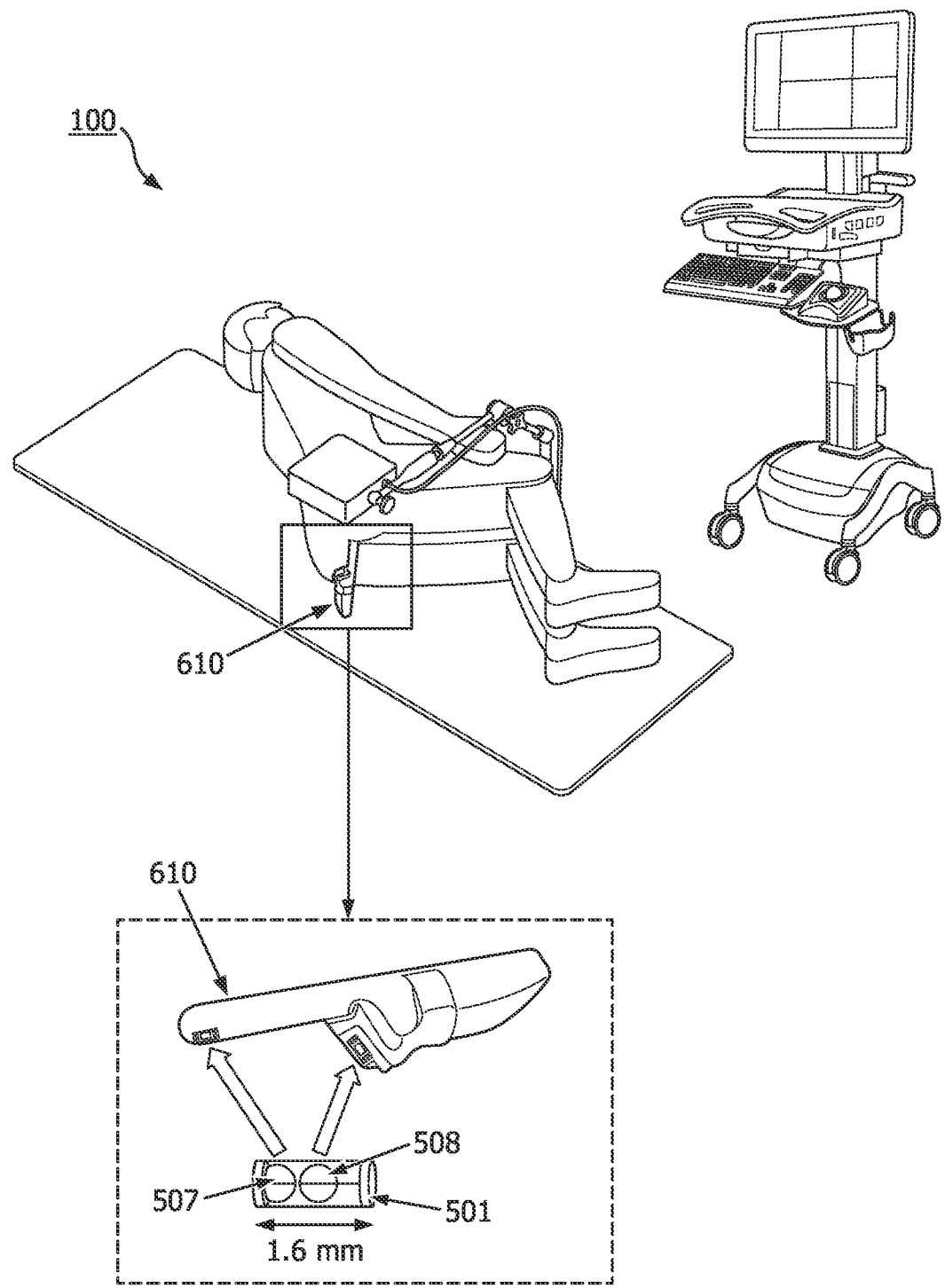
FIG. 4 shows schematically and exemplarily a further implementation of the marker device in a tracking system for tracking a medical device.

To that end, FIG. 4 shows at least one marker device 501 that is attached to an ultrasound probe 610 to track the position of said ultrasound probe 610 during an ultrasound measurement on a patient 100.

Figure 5A:
FIGS. 5A and 5B show schematically and exemplarily a further implementation of the marker device in a tracking system for tracking a medical device.
Figure 5B:
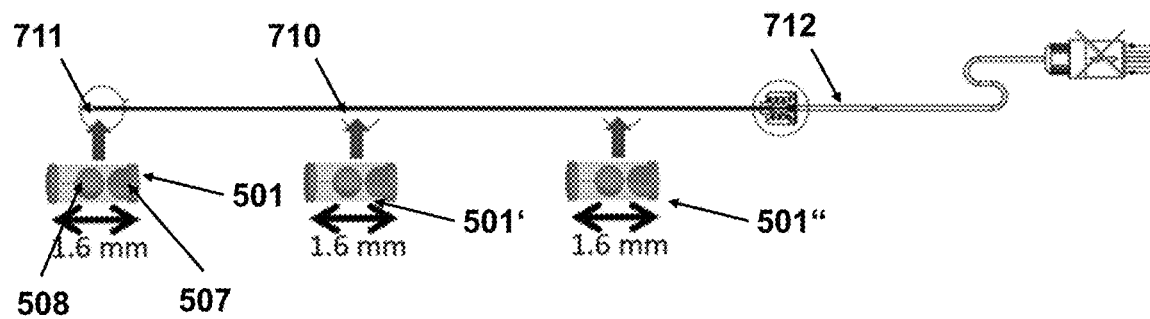

FIG. 5A illustrates a marker device 501 as described above being attached to a stylet 710 which is used for being introduced into a patient's tissue. In the embodiment of FIG. 5A, a single marker device attached to a first end portion 711 of the stylet 710 is used for keeping track of the stylet upon introduction into the patient's tissue. Alternatively, as illustrated in FIG. 5B, a plurality of marker devices 501, 501', 501" may be attached to stylet 710 along a length of stylet 710 from a first end portion 711 to a second end portion 712. This plurality of marker devices 501, 501', 501" may allow to track the position of the stylet 710 relative to the coordinate system provided by the tracking system, but may also allow to determine the orientation and/or shape of the stylet 710.

Figure 6:
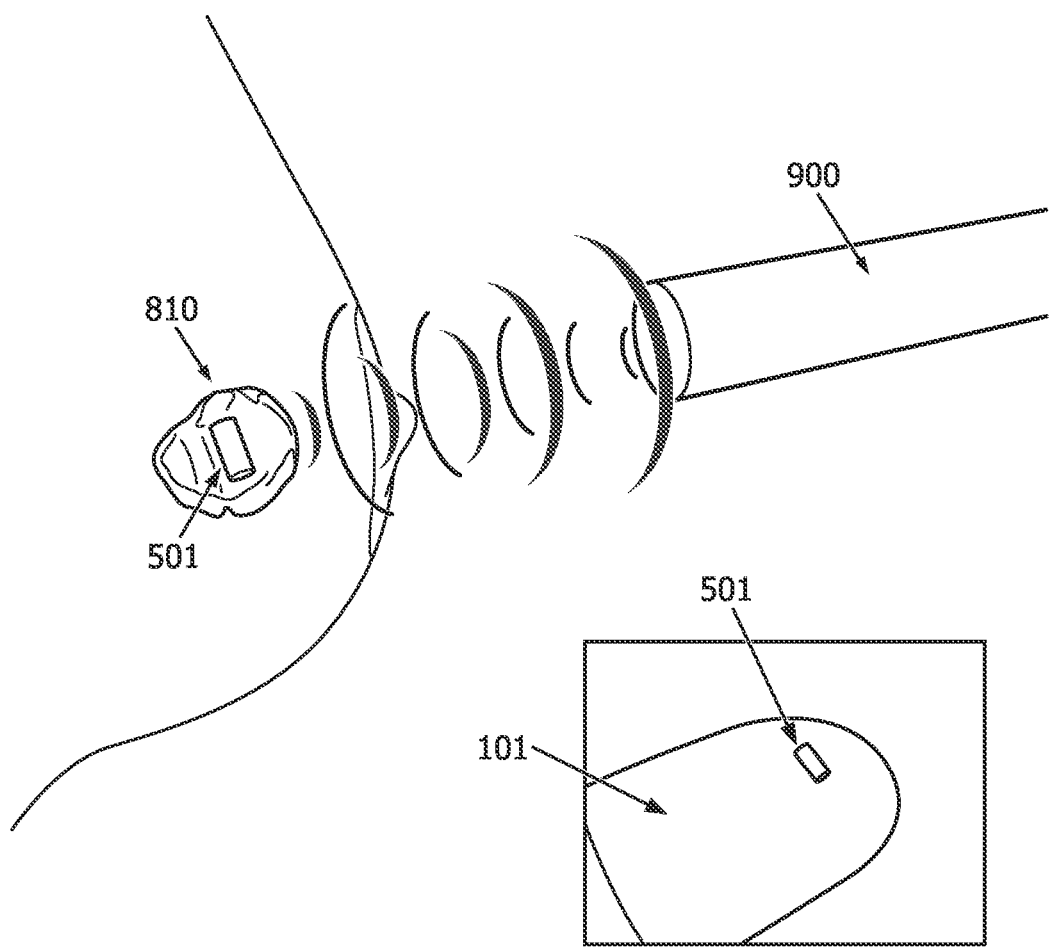
FIG. 6 shows schematically and exemplary an implementation of the marker device and tracking system for determining the position of a tumor.

FIG. 6 schematically illustrates the use of a marker device 501 for tracking of tissue. More specifically, in the exemplary embodiment of FIG. 6, the marker device 510 is used to determine the position and/or orientation of a tumor 810. A position determination unit 900 of the tracking system is then used to determine the position of the marker device, and, hence, the tumor 810 relative to the coordinate system provided by the tracking system (not shown). This may allow to more accurately localize the tumor 810 for subsequent removal. For illustrative purposes of the dimensions of the marker device 501 used for tumor localization, FIG. 6 further shows the marker device 501 in relation to a human finger 101. As may be appreciated from this illustrative representation, the marker device 501 has minimal dimensions while at the same time providing for accurate localization.

Figure 7:
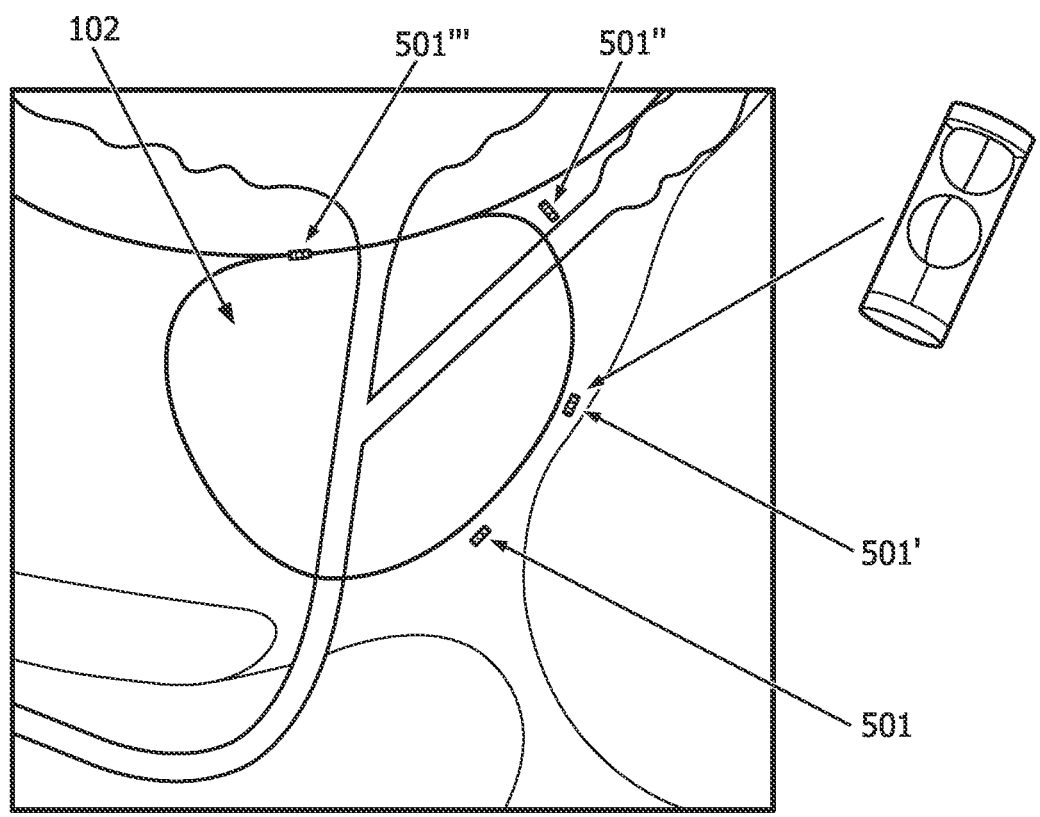
FIG. 7 shows schematically and exemplary an implementation of multiple marker devices and a tracking system for determining the position and/or orientation and/or shape of a region of interest in a patient's tissue.

FIG. 7 schematically shows another illustrative embodiment for employing one or more marker devices 501, 501', 501", 501'" for performing position determination as well as for therapy control during a medical treatment performed on a patient. In such a case, the information provided by the marker devices 501, 501', 501" and 501'" attached to a prostate 102 of a patient is combined with information from additional sensors, such as a pressure sensor, a temperature sensor, a radiation sensor or the like. This combination allows to determine the position and/or orientation of the prostate 102 relative to the coordinate system provided by the tracking system and to further measure, using the above mentioned sensors, parameters such as temperature, pressure or radiation, whereby these measurements may be correlated to specific positions. This allows to obtain a spatial mapping of these measured parameters. Such a spatial mapping may allow for controlling and/or monitoring the course of a treatment procedure.

Specifically, FIG. 7 shows a prostate 102 of a patient. In the specific embodiment according to FIG. 7, an ablation procedure shall be performed on the prostate tissue. For that purpose, a plurality of marker devices 501, 501', 501" and 501'" is provided at several positions of the prostate 102. Further, one or more temperature sensors (not shown) are provided at different positions of the prostate, preferably close to the region of interest at which the ablation treatment shall be performed. This allows to provide a spatial mapping of the temperature development during the ablation treatment and may help to avoid temperature-induced damages to healthy tissue and/or an overtreatment during the ablation procedure.

Figure 8:
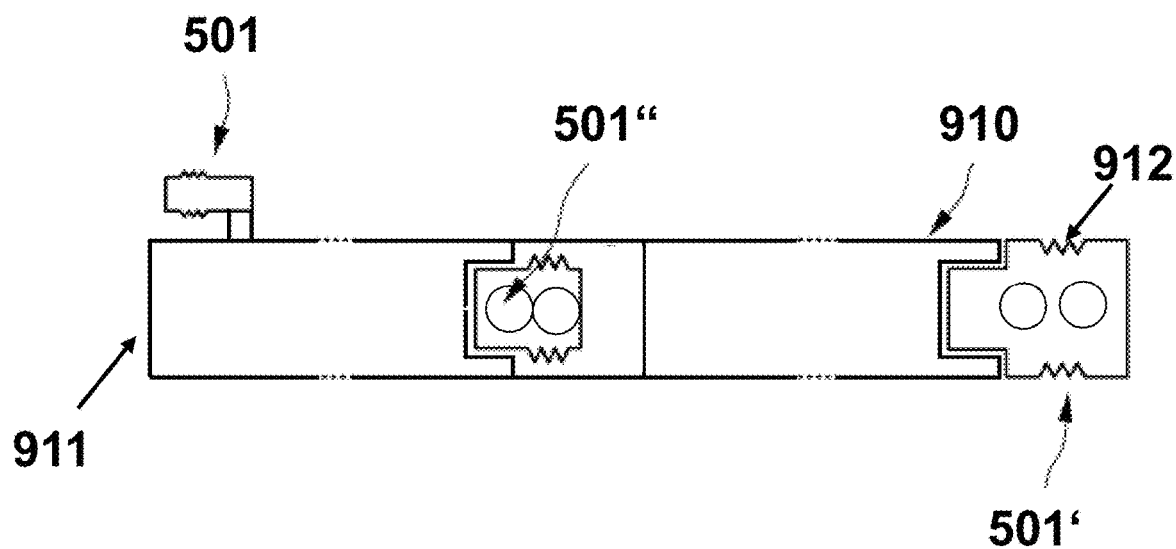
FIG. 8 shows schematically and exemplarily an embodiment of a medical device corresponding to a wire for treating of brain aneurism to which a marker device is attached.

FIG. 8 shows schematically and exemplarily an embodiment of a wire for treating of brain aneurism. The wire 910 comprises one or more marker devices 501, 501', 501" in accordance with the described embodiments. In particular, a first marker device 501 at a first ending portion 911 of the wire 910 at one side of this first ending portion 911. Moreover, a further marker device 501' can be attached to a second ending portion 912 of the wire 910 and within an intermediate section of the wire 910 a further marker device 501" can be mounted, wherein the wire 910 can comprise an inner cavity in which the marker device 501" is arranged.

Figure 9:
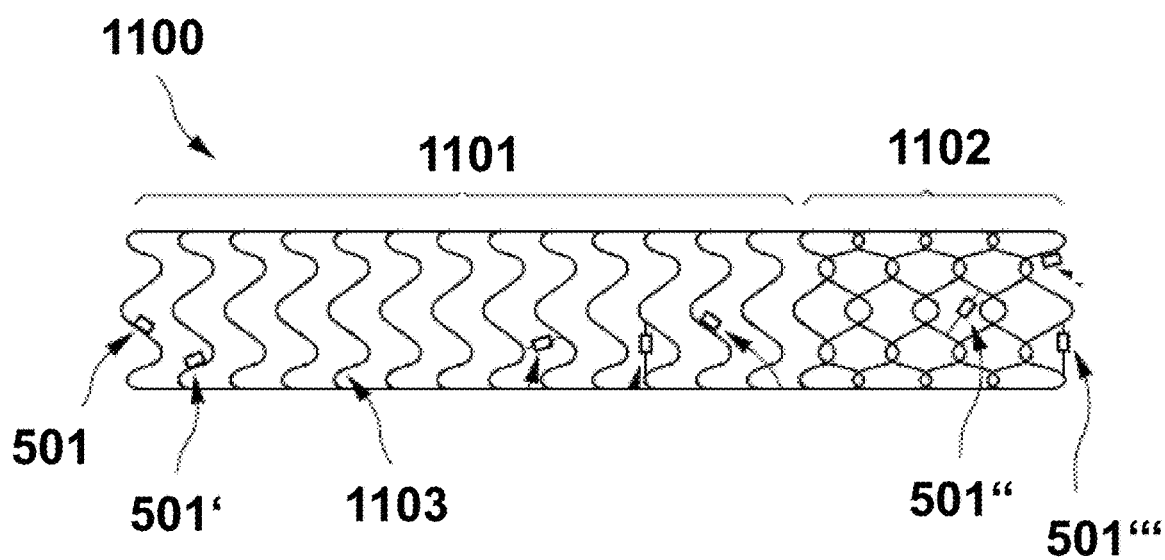
FIG. 9 shows schematically and exemplary an embodiment of a medical device corresponding to a hepatic shunt device to which a marker device is attached.

FIG. 9 schematically and exemplarily shows an embodiment of a hepatic shunt device 1100 comprising a wire structure 1103. In this embodiment the wire structure 1103 has a first part 1101 surrounded by a lining material and a bare second part 1102. In this embodiment the first part 1101 is lined by using PTFE (polytetrafluoroethylene). Moreover, in this embodiment the first part 1101 of the wire structure has separate wires, whereas in the second part 1102 of the wire structure 1103 the wires are interwoven. The hepatic shunt device 1100, which might also just be named hepatic shunt, comprises several marker devices 501, 501', 501", 501'". For instance, a first marker device 501 is arranged next to a respective wire of the first part 1101 of the wire structure 1103 inside the PTFE tube. A second marker device 501' is arranged "in wire" within the PTFE tube, i.e. the marker device 501' is arranged between two ends of a respective wire of the wire structure 1103. Further, a third and fourth marker device 501", 501'" are arranged at the second part 1102 of the shunt device. By arranging the marker devices along the length of the shunt device, its position and/or orientation may be determined. Further, the shape of the shunt device 1100 may be determined.

It should be noted that in FIGS. 4 to 9 the arrangements of marker devices are only exemplarily, i.e. also more or less marker devices can be arranged at the same or other positions at or within the respective medical device and/or element. It is also possible that the respective device only comprises a single marker device. The one or several marker devices attached to the respective medical devices and/or elements are marker devices in accordance with at least one of the described embodiments.

In the following, it is assumed that the length of the marker device is always about twice the diameter. All devices with a diameter of 0.3 mm or larger will enable real-time tracking (more than 10 readings per second) at a distance of more than 30 cm with a high accuracy.

The marker device can be attached to a guidewire, for instance, as explained above with reference to FIGS. 2 and 3 and used for tracking such guidewire. Further, the marker device could be used for tracking a catheter. A marker device could also be placed on a stent. To minimize disturbances due to the marker device during stenting, the marker device should be as small as possible, and should not exceed stent wire diameters. Typical stent wire diameters are between 0.2 and 0.5 mm. Thus this would be a useful range for marker device diameters. It is also possible to inject a marker device with a syringe, wherein the marker device can be stuck into a smaller vessel in the pulmonary or hepatic areas without risk to the patient. Typical diameters for injection would be between 0.3 and 1.0 mm.

The described marker devices are preferentially configured to compensate a dependence of the resonance frequency on the temperature. One possible for compensating temperature-based shifts of the resonance frequency will in the following be described with reference to FIG. 10.

Figure 10:
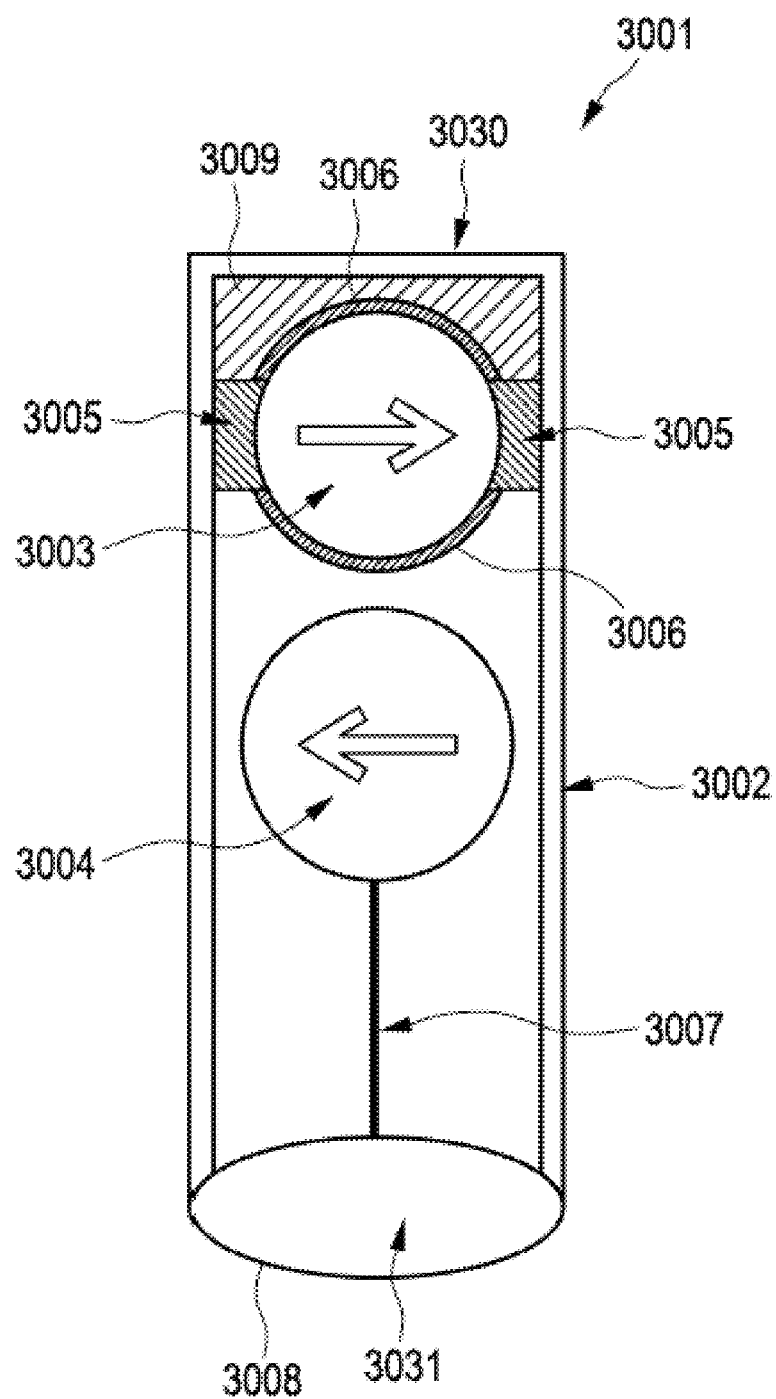
FIG. 10 shows schematically and exemplarily an embodiment of a marker device with temperature compensation.

Also in FIG. 10 the marker device 3001 comprises a casing 3002 and a magnetic object 3004 being arranged within the casing 3002 such that it is rotatable out of an equilibrium orientation if an external magnetic torque is acting on the magnetic object 3004. The marker device 3001 further comprises a restoring torque unit 3003 being adapted to provide a restoring torque to force the magnetic object 3004 back into the equilibrium orientation if an external magnetic or electromagnetic field has rotated the magnetic object 3004 out of the equilibrium orientation, in order to allow for a rotational oscillation of the magnetic object 3004 excited by the external magnetic or electromagnetic field resulting in a respective magnetic torque. In this embodiment the casing 3002 is cylindrical and the magnetic object 3004 is rotatable around a virtual rotational axis centrally traversing the magnetic object 3004, wherein the magnetic object 3004 is rotationally symmetric with respect to the virtual rotational axis. In particular, in this embodiment the magnetic object 3004 is a magnetic sphere.

The restoring torque unit 3003 comprises a further magnetic object 3003 for providing the restoring torque. In particular, the magnetic object 3004 is attached to one end of an attachment portion, such as a filament, 3007, wherein another end of the attachment portion 3007 is attached to the casing 3002. The attachment portion 3007 is adapted to prevent the magnetic object 3004 from touching the further magnetic object 3003 due to their magnetic attraction and to allow the magnetic object 3004 to rotationally oscillate. In this embodiment the further magnetic object 3003 is fixedly attached to the casing 3002 by using glue 3009.

The magnetic object 3004 forms a first magnetic dipole, the further magnetic object 3003 forms a second magnetic dipole and the magnetic object 3004 and the further magnetic 3003 are arranged such that in the equilibrium orientation the first and second dipoles point in opposite direction. The first magnetic object 3004 and the second magnetic object 3003 are permanent magnets, wherein in the equilibrium orientation a north pole of the magnetic object 3004 faces a south pole of the further magnetic object 3003 and vice versa.

The casing 3002 is cylindrical, wherein the cylindrical casing 3002 comprises two end surfaces 3030, 3031 and wherein the further magnetic object 3003 is fixedly attached to a first end surface 3030 and the end of the filament 3007, which is opposite to the end attached to the magnetic object 3004, is attached to a second end surface 3031 of the cylindrical casing 3002.

In this embodiment the second end surface 3031 of the casing 3002 is formed by hard wall 3008 of the casing 3002, wherein the magnetic object 3004 is attached to the hard wall 3008 via the attachment portion 3007 such that external pressure influences are not transferred to the inside of the casing 3002.

The marker device 3001 further comprises magnetic material 3005, 3006 arranged adjacent to the further magnetic object 3003. This magnetic material 3005, 3006 influences the magnetic field generated by the further magnetic object 3003, wherein the influence of the magnetic material 3005, 3006 depends on the temperature in order to change the strength of the magnetic field at the position of the magnetic object 3004 and hence in order to change the resonance frequency if the temperature changes. The magnetic material 3005, 3006 is adapted such that its magnetization decreases with increasing temperature. Moreover, the magnetic material 3006 is adapted such that its magnetization direction is opposite to the magnetization direction of the further magnetic object 3003 and the magnetic material 3005 is adapted such that its magnetization direction and the magnetization direction of the further magnetic object 3003 are the same. The magnetic materials 3005, 3006, which are soft magnetic materials, therefore influence the resonance frequency depending on the temperature in opposite frequency directions, i.e. one of these magnetic materials leads to a change towards higher frequencies depending on an increasing temperature and the other of these magnetic materials leads to a change towards lower frequencies with increasing temperature.

The marker device 3001 is thus preferentially configured such that the resonance frequency does not depend on the temperature. In order to compensate any unwanted temperature dependent frequency shifts, the magnetic materials 3005, 3006 can be tailored such that they provide the same frequency shift in an opposite frequency direction depending on a temperature change. In particular, the magnetic materials 3005, 3006 can be chosen and arranged such that any temperature dependence of the resonance frequency of the marker device 3001 is eliminated. It is also possible that only one of the magnetic materials, i.e. only a magnetic material decreasing the resonance frequency with increasing temperature or only a material increasing the resonance frequency with increasing temperature, is used for reducing or even eliminating the temperature dependence of the resonant frequency of the marker device 3001. One or both of the magnetic materials 3005, 3006 could be regarded as being compensation elements for compensating the temperature-induced shift of the resonance frequency.

Figure 11:
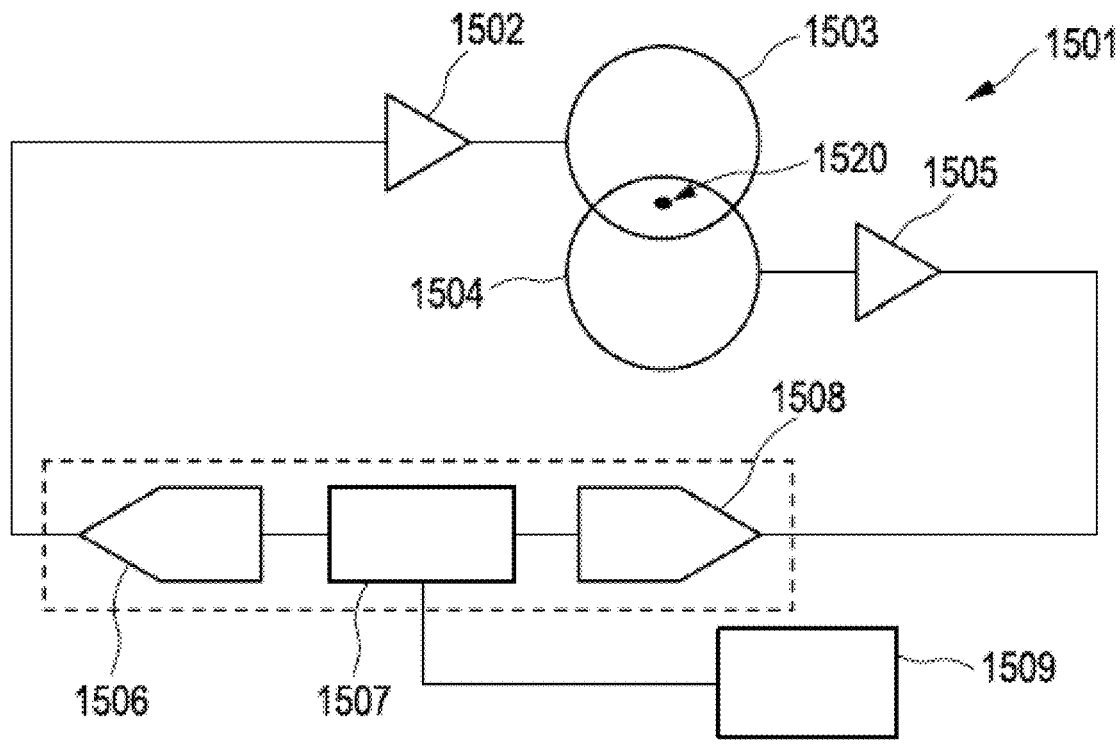
FIGS. 11 and 12 show schematically and exemplarily a tracking system for tracking a marker device according to an embodiment of the invention.
Figure 12:
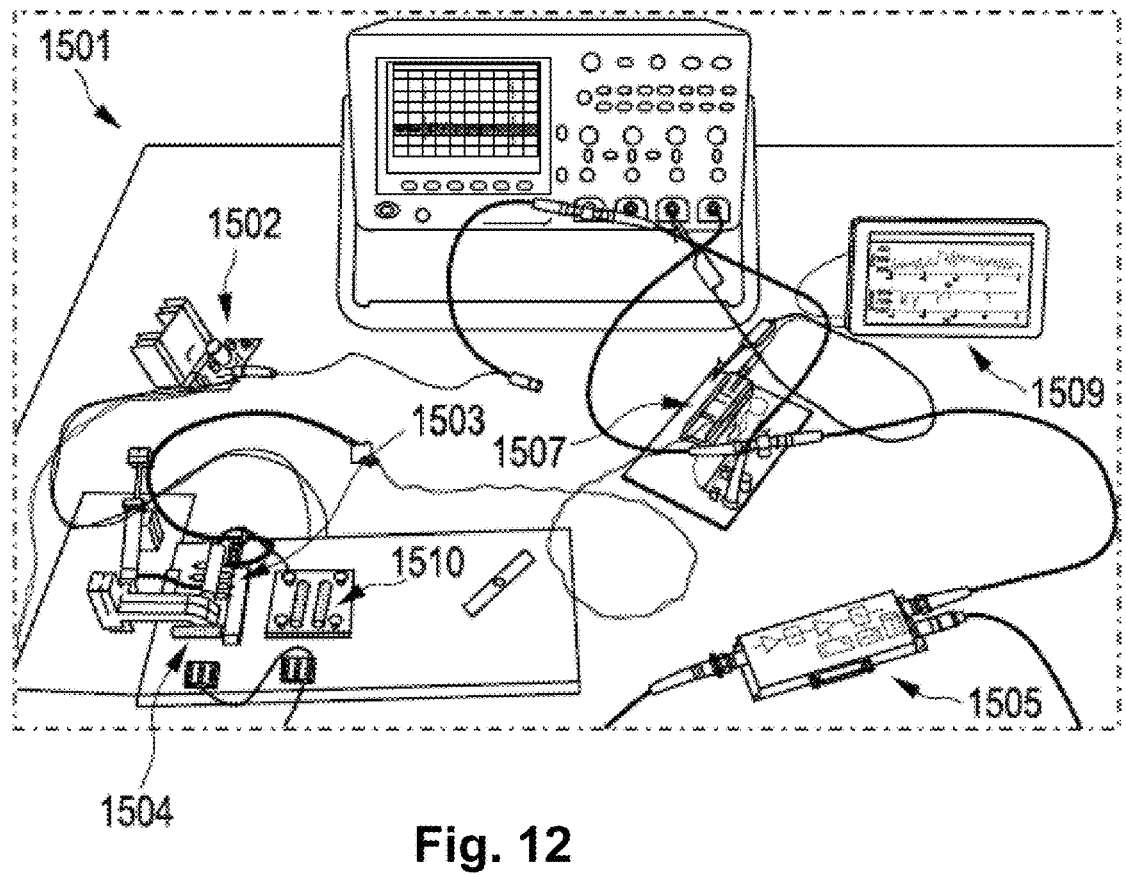

FIG. 11 schematically and exemplarily illustrates a tracking system 1501 for tracking a marker device as previously described, i.e. a tracking system for wirelessly determining the position and/or orientation of the marker device—attached to a medical device—based on one or more electrical response signals which are indicative of the response frequency of the oscillation of the magnetic object in the sensing unit. FIG. 12 shows exemplarily a prototype of the tracking system 1501. The tracking system 1501 comprises basically at least one field generator of magnetic fields and at least one magnetic field sensor, i.e. a transducer for transducing a magnetic or electromagnetic field generated by the induced oscillations of the magnetic object of the sensing unit into electrical response signals.

The operation frequency band is in the low kHz range and has to be broad enough to cover the responses of several sensors operating in parallel at different frequencies, and possibly also higher harmonics of the sensor resonance frequency as well, e.g. to improve SNR. The transmit field amplitudes are at maximum a few milli-Tesla, whereas field amplitudes to be detected are between $1/10$ of a nT and several nT. Many different field generators may work (oscillating permanent magnets, coils with cores/without cores, magnetostrictive field modulators, . . . ) as well as many different magnetometers (Hall effect, various kinds of magneto-resistive sensors, magneto-resonance sensors, SQUIDS, etc.). The technical simplest systems are coreless conductor loops for sending and receiving of magnetic fields. Coils are generally good enough for the sensor application. The coil for generating the magnetic field can be also used for receiving the magnetic field. However, different coils can be employed for these tasks, which gives some advantage.

In FIG. 11 the tracking system 1501 comprises a transmit coil 1503 which is connected to a microcontroller 1507 via a digital-to-analog converter 1506 (DAC) and an audio amplifier 1502 for generating the external magnetic or electromagnetic excitation field for the marker device 1520 which can be embodied as described before. A receive coil 1504 is also connected to the microcontroller 1507 via a low noise amplifier 1505 and an analog-to-digital converter 1508 (ADC) for reading out the resonance frequency. The microcontroller 1507 is connected to a display computer 1509. The microcontroller 1507 is configured for, for instance, signal generation and reception, frequency evaluation and control. In FIG. 12 also a transmit/receive decoupler is shown.

Figure 13:
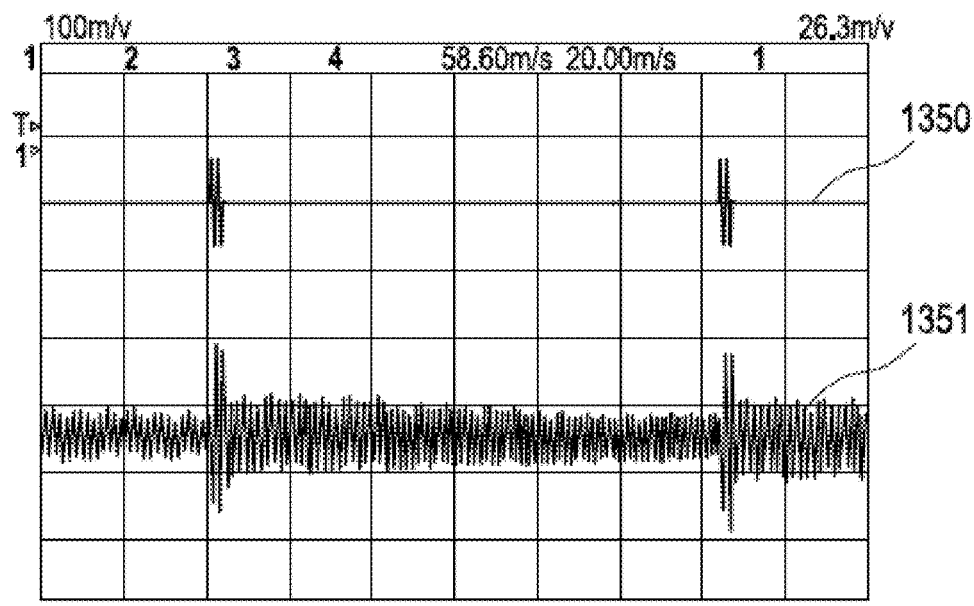
FIG. 13 shows schematically and exemplarily excitation pulses and resulting induced voltages.

The microcontroller 1507 generates transmit pulses (cf. upper trace 1350 in FIG. 13) that are amplified using the audio amplifier 1502 and then passed to the transmit coil 1503 which can also be named excitation coil. In this implementation, a separate receive coil 1504 is employed, which is decoupled from the transmit coil 1503 using two additional decoupling coils 1510 which are not shown in FIG. 11 for clarity reasons. The receive signal is fed into the low-noise amplifier 1505 and passed to the ADC 1508 of the microcontroller 1507, where a time trace of typically $1/20$ of a second is sampled at a rate of about 20 kS/s. FIG. 13 shows, besides the transmit pulses 1350, which could also be named excitation pulses, the induced voltage 1351 in the receive coil 1504 due to sphere oscillation in the sensor and hence due to sensor response. The spacing of the excitation pulses 1350 might be continuously adjusted by the microcontroller 1507.

In the embodiments described herein, the tracking system may particularly correspond to a multi-coil system. The use of several coils enables position determination for the marker device by determination of position and orientation of the oscillating magnetic dipole in space. The different amplitudes of the receive signals together with the known coil element sensitivities can be matched to a dipole model for determination of the position and orientation parameters. An example of a multi-coil system for implementation in a pillow or mattress is displayed in FIG. 14. With many receive coils and channels available, the additional information can also be used for improving background signal suppression as described further below.

Figure 14:
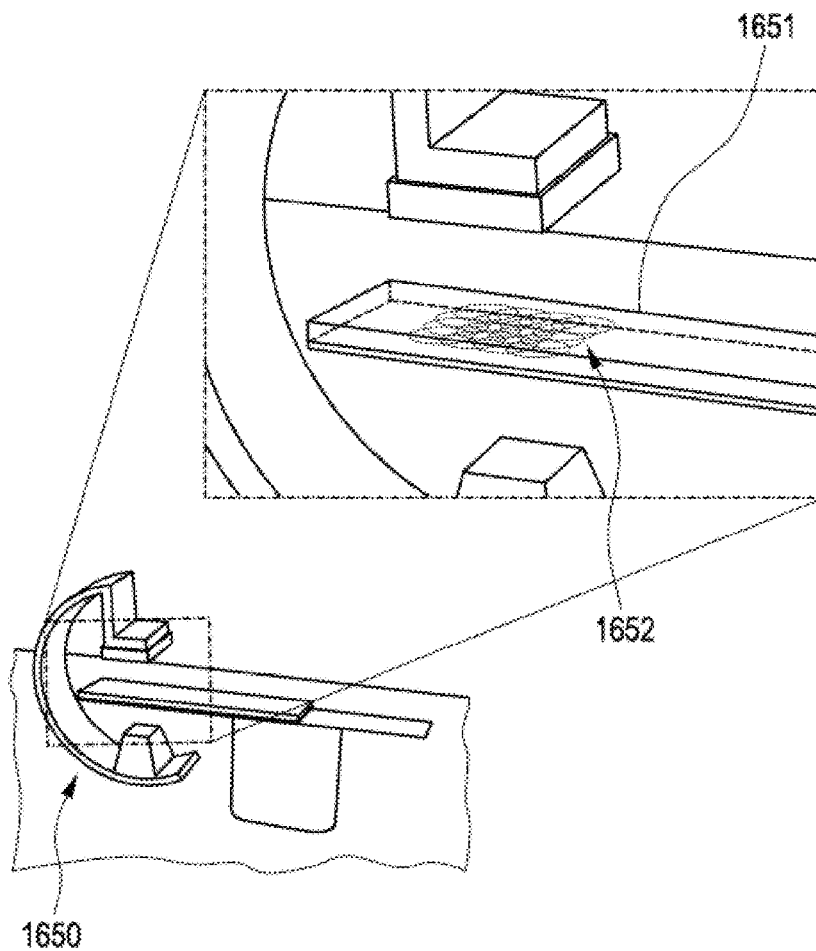
FIG. 14 shows schematically and exemplarily a multi-coil array integrated in a mattress of a patient bed of an imaging system.

In FIG. 14 the several coils 1652 form a multi-coil array which is integrated in a mattress 1651 of a patient bed of an imaging system 1650 like a C-arm system. The coils 1652 are preferentially aluminum coils having an x-ray absorption of less than 10 percent. It is therefore not required to increase the patient dose, if the coils 1652 are used.

In the following the coil-based transmit system of the tracking system will be exemplarily described in more detail. The coil based send system comprises the send amplifier and the send coil. Optionally there is also a matching circuit and a "mute" circuit involved. As the send signal shape is not very critical in the sensor application, a multitude of amplifiers are suitable for the task (Class A, Class B, Class AB, Class D, etc., employing transistors, vacuum tubes, thyristors, and many more components). As the signal quality is not critical, the amplifier topology with the lowest loss can be selected, which is a half or full bridge amplifier employing switches with low on-resistance. The preferred switches are MOSFETs or IGBTs. The matching circuit is in the simplest case a simple capacitor in series to the inductor. Provided the amplifier operates with sufficient supply voltage, such a matching capacitor may be omitted or the capacitance may be chosen so high that the resonance frequency of coil with capacitor is well below the operation frequency. The matching circuit is of interest for another reason. Medical equipment should operate always in a safe way and reducing voltages is of concern. By placing the capacitor in the middle of the coil, so that the current flows through one coil section, then through the matching capacitor, and afterwards to the second coil section, the peak voltage differences can be reduced. This is even more true, if the coil is split into more sections each connected with the appropriate capacitor. This makes the coil and matching circuit to a combined unit. The field amplitude is conveniently controlled by a pulse width modulation, i.e. the amplifier increases/decreases the current through the coil only for a fraction of the cycle or alternates rapidly between increasing/decreasing of the current. As the exact signal shape is less relevant for the sensing application, it is best achieved by only changing state 2 times within a half wave (or 1 time in case of full power where the pulse length is identical to the half wave length). Ideally, the amplifier has not only the possibility of increasing or decreasing the current but also to keep the current more or less constant or at the level the matching circuit dictates. This is achieved by a proper switching sequence of the transistors in the half or full bridge. Generally, the supply voltage of the amplifier should be rather low and lie in the range below 50 V. In addition, the matching circuit should be set-up in a way to not exceed this 50 V limit at any two points. It is even better not to exceed 24 V in both cases. This means that the number of windings should be kept low. However, peak operation currents should exceed 10 A, better 100 A.

In the following a send/receive insulation will be described. It is essential that not too much noise from the send system, i.e. from the field generator, couples into the receive system, i.e. into the transducer for transducing the magnetic or electromagnetic field generated by the induced mechanical oscillations of the magnetic object of the sensing unit into electrical response signals, while the send system is not in the send mode, i.e. no excitation field is generated. In addition, the send amplifier should not short the receive signal or even partially reduce it. There are several possibilities to achieve this. If we have different send and receive coils, the two coils could be decoupled geometrically (cf. FIG. 15).

Figure 15:
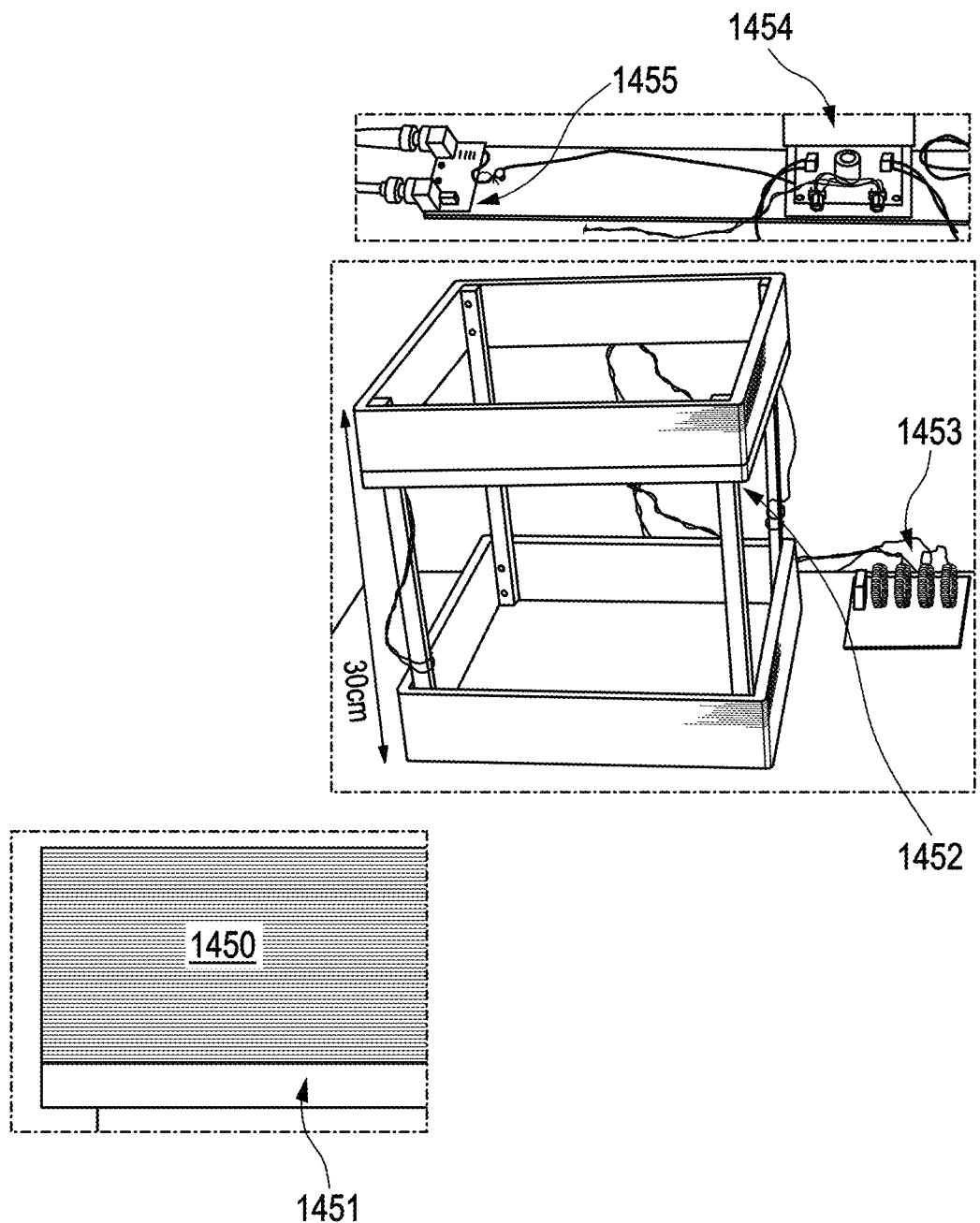
FIG. 15 illustrates schematically and exemplarily receive coils of the tracking system for detecting the magnetic or electromagnetic field variation induced by the mechanical oscillations.

FIG. 15 shows an implementation of a gradiometric receive coil design for suppression of transmit and background signal in the receive path. Here large coils 1452 have been chosen, which enables tracking the marker device up to distances of about 30 cm above the upper coil. The gradiometric design uses the geometric decoupling method: the transmit coil loops 1451 are connected to produce parallel fields, whereas the receive coil loops 1450 are connected to receive field gradients and suppress homogeneous fields. This transmit and receive system provides an intrinsic geometric decoupling by using parallel transmit loops and anti-parallel receive loops, wherein this might be named gradiometer configuration. This leads to an intrinsic geometric coupling. This system with the air coils is highly linear. FIG. 15 also shows a DC block 1455 with an audio amplifier 1454, and a low pass transmit filter 1453. The lower part of FIG. 15 illustrates outer windings of the receive coil 1450 and inner windings of the transmit coil 1451.

In particular, in FIG. 15 the lower left image is a close-up of the middle portion of the upper coil assembly. In the lower left image, one can see actually only 1 turn of the send coil 1451 peeking out in the bottom. The rest is obscured by the receive coil, wound with a much thinner wire. The DC blocking circuit 1455 is just a signal conditioning in front of the audio amplifier as the signal for the audio amplifier may be generated by a simple PWM output. The low pass filter 1553 is a filter in between the output of the audio amplifier 1454 and the transmit coil 1451. It has two purposes. First avoiding the introduction of high frequency noise, second it is there to combine the two output channels of the audio amplifier into one.

A geometric decoupling is not always possible, especially if an array of senders and receivers is used. In this case a transformer can be introduced with terminals connected to the send circuit as well as to the receive circuit. This transformer provides the decoupling of the send and receive system. This transformer solution can be used even if a combined send/receive coil is used. The transformer may be substituted by a capacitive (or even resistive) decoupling network both with combined and separate send/receive coils. The drawback of the compensation methods is that they need quite some space, add noise and in the case of capacitive decoupling narrow the frequency operation range of the tracking system. A more robust and cheaper solution is to add a circuit that completely mutes the send amplifier during receive times. For this, crossed diodes can be added to the output of the amplifier. Especially diodes with low capacitance at zero voltage like PINdiodes are useful. This provides a high impedance if no current flows. To further augment this, an electronic switch can be placed at the output of the amplifier, shorting all residual noise signals while receiving. The diodes still provide the desired high impedance. It is also possible to construct a special amplifier that is totally noise free and provides a high impedance when not operating. With the half and full bridge designs, this can be achieved by having absolutely no switching operation in any component during receiving, the use of low output capacitance transistors, by having about half the supply voltage at the output(s) in receive mode, having no noise coming from input connectors (optical insulation), and having a highly filtered supply voltage (heavy filtering or no power supply switching during receive operation).

In the following the coil-based receive system of the tracking system will be discussed. The receive amplifier should be of a low noise type. However, the requirements are not so high that uncommon receive transistors need to be used. Standard low noise bipolar or JFET silicon transistors are usually good enough. The only special features are that the amplifier needs to survive the send pulses and starts operation shortly after the send pulse. There are several ways to reach this goal. In the case of decoupled send/receive systems (including combined send/receive coil with decoupling network), the receive amplifier needs no special features to reach this goal. If no decoupling is present, the amplifier can be hardened to the send pulse. This can be done by adding a suitable capacitor to the input of the amplifier and crossed diodes to the second terminal. This provides a suitable high impedance in the send case and shorts all to high voltages to harmless levels for the amplifier. Naturally, the added capacitor needs to be rated to the maximum send voltage. The capacitance value needs to be so high, that the signal at the amplifier is not too much reduced in the receive case. For a JFET based amplifier, this is generally not a critical issue. The crossed diodes can be augmented or supplanted by a suitable electronic switch, like an optocoupler with MOSFET output. This has the advantage to further reduce the input voltage. If properly done, the receive amplifier will not be saturated and functions right after the send signal has declined sufficiently.

In the following the interface to the digital system will be discussed in more detail, wherein firstly the digital signal output and processing is described. Although an analog timer system could generate the output signals, usually a digital system, like a DSP or FPGA, will be used. Depending on the type of output amplifier different outputs may be used. For an analog amplifier, some type of ADC may be used. As the output signal quality is not very critical, a simple PWM type of analog output may be sufficient. Digital amplifiers are best interfaced using a digital output line. However, it is also possible to use an analog output for them and implement the switching pattern generator on the amplifier. With the best matching amplifier, the half or full bridge, it is most suitable to produce the switching pattern directly on the digital system. In addition, also the switching patterns for receive amplifier input protection and send amplifier output denoising may be generated directly by the digital system. The common feature to all the output options is, that they need to be fast enough to exactly keep phases over different excitations of a single marker device or between different marker devices. So the output needs to have the possibility of switching updates on a raster finer than a 10th of the full period time, better finer than a 100th of the full period time. For a say 2 kHz sensing device, this means updates on a raster finer than 220 kHz, even better 200 kHz. This does not mean that every time at the raster points switching state changes need to be possible. So it is for example possible to have a serial interface for each amplifier that transfers the new switching state to the amplifier and a protocol to execute this change at a certain time over the same serial interface. This is especially useful for the amplifier type that inherently goes silent during the receive phase. For this a 1 bit serial interface can be implemented which only needs a single optocoupler on the amplifier. This makes it easy to reach noise immunity from the digital send side, as the stray capacitance in a single optocoupler can be very low.

In the following, the analog to digital interface will be discussed. The analog to digital conversion is fairly standard. As the signal is low bandwidth, at least if only a single marker device is used, it would be possible to mix the signal down to near DC and sample this signal. However, the signal from the marker device has a rather low frequency, usually below 10 kHz. Today, there are plenty of suitable ADC chips to sample this directly. Especially, as digital signal processing is crap in comparison to analog filters, it is best to use a heavily oversampling in the ADC. At least 10 times the frequency of the marker device should be used bit 100 or 1000 times are also valid choices. The high oversampling makes the design of the ADC input filter easy and cheap as only the sensor signal frequency needs to come through while above the Nyquist frequency no signal shall come through. However, a filtering below the sensor frequency is also useful to avoid the usual high background signals there. A high background signal may reduce the possible amplification prior to the ADC, increasing ADC noise contribution. The ADC noise (number of effective bits) and samples should match the needed dynamic range and noise expectations. This means, the ADC should not be in saturation while the maximum expected signal and all noise components are present. Simultaneously, the quantization noise of the ADC should be so low, that the overall noise is not increased. Here noise means all the unwanted components in the recorded signal stemming from real noise sources like the coils resistance or the receive amplifier behavior. It also includes the interference components that cannot be eliminated by suitable filtering and background signal subtraction. Usually, with modern ADC chips this requirement can be meat e.g. with 2 MS/s 18 Bit ADCs. For cost savings, it may be useful to employ an ADC with lower specifications but add a gain control to still reach good overall performance.

In the following the data processing will be discussed. Before data evaluation the raw ADC data have to be processed. As heavy oversampling is desired, a first processing step could be a decimation step. This has the main advantage to reduce the data size and therefore the needed computing power for further steps. Optionally the decimation step may include other filters i.e. a band pass around the expected signal frequency. This may simplify further processing steps and reduce the dynamic range of the signal which in turn may save computing power (variables with less bits). A further optional data processing step is to apply an inverse non-linear filter to reduce the non-linearity of the receive system. This means, the non-linearity of the full receive system is measured and a computational filter is constructed to reverse the effect of the non-linearity. This is especially useful if low cost components are used because they tend to have more non-linear behavior.

This non-linear filter may alternatively be used as the first processing step. If more than one receive signal is used, there are further signal processing steps. If at least one receive channel is not detecting the signal from the sensing unit and thus provides a measure of the background signal, this (and all other such signals) are correlated with the receive signal and the correlating components are subtracted from the signal bearing channels. This subtraction can be done in time or frequency domain or a mixture of both. If there are no channels without signal from the sensing unit, a data processing strategy sometimes called "virtual gradiometer" can be used. This decomposes the multitude of channels in virtual channels that are linear combinations of the physical channels to minimize interference of signals not generated by the sensor. The factors for the linear combinations may be found by correlating the signals of the channels excluding the signal band of the sensing unit(s).

Moreover, in the following the data evaluation will be explained. Frequency is the main parameter to be extracted from the acquired signal from the sensing unit signal. Due to the high quality-factor of the resonator (time constant up to seconds), the subsequent excitation pulses are typically played out before the oscillation has fully decayed (cf. FIG. 13) and thus need to have the correct phase and timing to amplify the existing oscillation. This requires real-time extraction of the frequency between subsequent excitations. The frequency can be extracted either using a comparison algorithm that minimizes the phase differences between the measured signal and pre-calculated time-traces spanning a range of frequencies or by Fourier analysis, which is the preferred method. High-resolution frequency information can be obtained by time-domain zero padding or frequency domain interpolation and subsequent localization of the resonance peak in the spectrum, either using a peak-finding or a curve fitting procedure. For further improvement of the frequency determination accuracy and reliability, the higher harmonics of the detected resonance signal can be incorporated into the evaluation (cf. spectrum in upper right of FIG. 16), e.g. using a weighted frequency estimation based on the several harmonics or by checking the consistency of the frequency determination between several harmonics.

Figure 16:
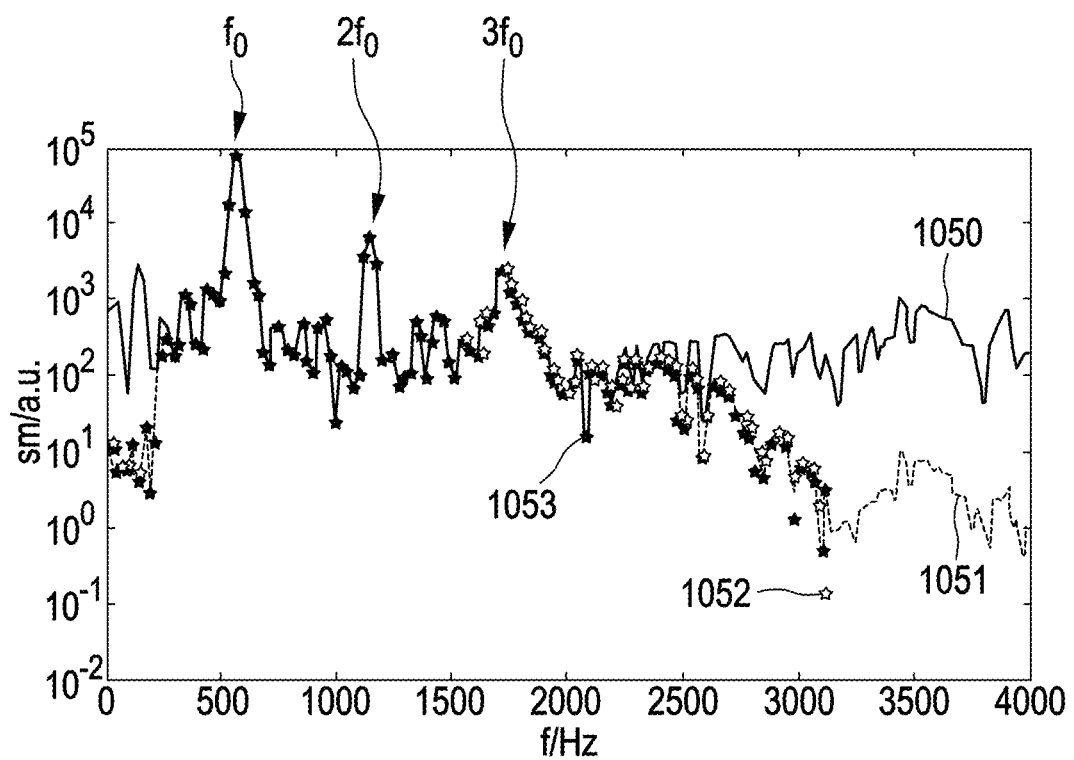
FIG. 16 shows a frequency spectrum used for determining the resonance frequency, FIG. 17 schematically and exemplarily shows an analog receive filter.

In the example, to which FIG. 16 refers, the signal of the second harmonics is an order of magnitude smaller than the base frequency signal. A better filtering is therefore required. Various filter stages can be used to optimize the signal at resonance frequency and higher harmonics thereof like analog excitation filters like DC block and low pass, analog receive filters like a band pass filters, and digital receive filters like IIR response filters for real time processing (sixth order Chebyshev type II). In FIG. 16 the center position of the f0 resonance peak is determined from the largest peak in the filtered spectrum. From f0, the timing of the next in-phase excitation pulses is calculated. The repetition frequency of the system is between 5 and 30 Hz, providing a real-time trace of the frequency response.

Figure 17:
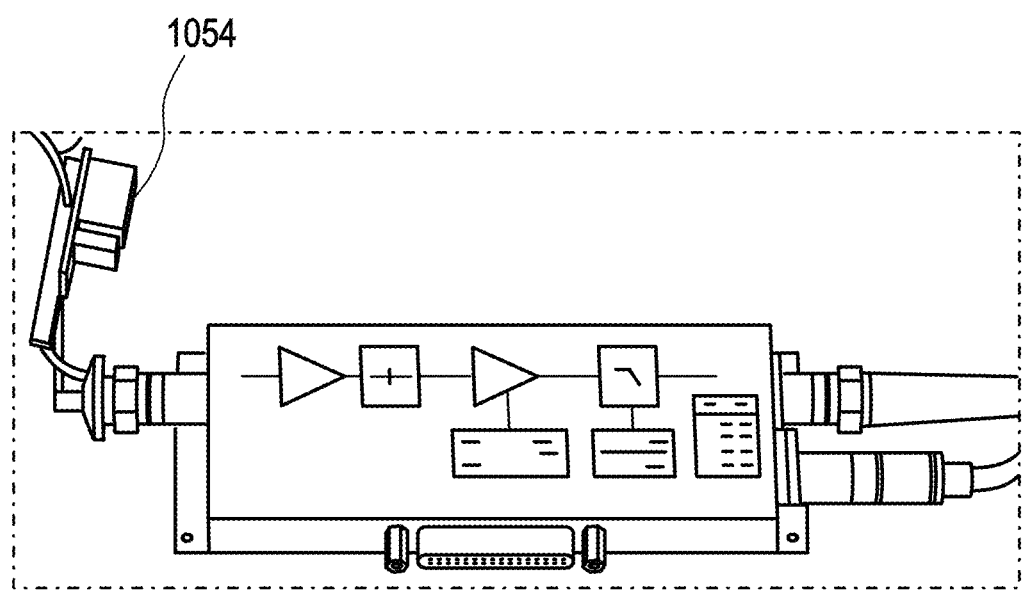
Figure 18:
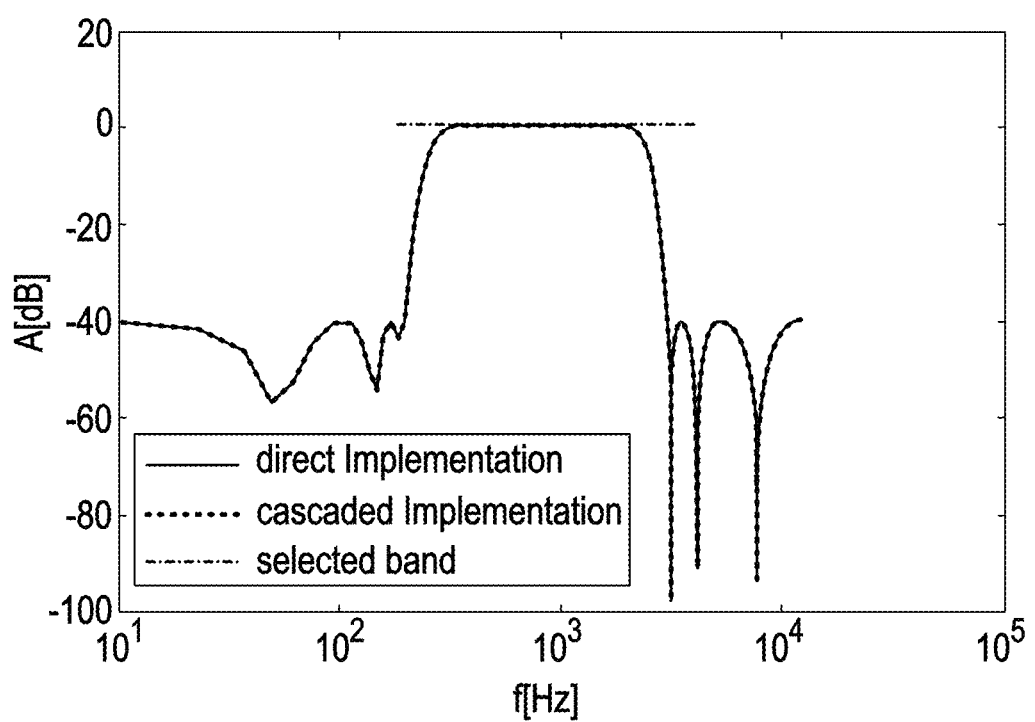
FIG. 18 illustrates exemplarily a Chebyshev type II band pass frequency response.

In FIG. 16 the signal spectrum is displayed with and without digital bandpass filtering (1051 vs 1050). The dotted points are in the range selected for evaluation. Different dot symbols represent different filter types which actually do not show a difference and can thus be ignored. In FIG. 17 the band pass is attached to a commercial low noise audio range amplifier, wherein the type is DLPVA-100-BUN-S of FEMTO Messtechnik GmbH. In FIG. 18 the actual 40 dB suppression spectrum of the digital filter is compared to the range of the selected band. The two implementations do not show a noticeable difference. The displayed filter is applied to the data shown in FIG. 16, leading to the difference between 1050 and 1051.

From the determined frequency and the known time stamp of the receive signals, the correct timing for the next block of excitation pulses can be calculated. The number and width of excitation pulses is adapted to generate an oscillation with sufficiently high amplitude to produce sufficient signal in the receive coils.

In the following, the process for determining the position of the marker device by means of a tracking system and, hence, for localization of a medical device to which a marker device is attached is described in detail. For such localization, frequency effects are either irrelevant (sensitivity encoding discussed further below) or negligible (gradient field encoding also discussed further below). For localization using the gradient field method which also acts on the sensor frequency, these compensations are not necessary, as there only the frequency change over a sub-second period of time needs to be evaluated. This change is not much dependent on the oscillation amplitude.

The signal of the magneto-mechanical oscillators is detected by the voltage $u_i(t)$ induced in a coil i as a result of the field variation due to the oscillatory motion of the magnetic moment m(t) of the suspended magnetic sphere at position $r_0$:

$$u_i(t) = -\frac{d}{dt}(B_{s,i}(r_0) \cdot m(t)) = \qquad (4)$$

$$-B_{s,i}(r_0) \cdot \frac{d}{dt} m(t) = -M_{sat} V_{sphere} B_{s,i}(r_0) \cdot \frac{d}{dt} \hat{m}(t),$$

wherein $B_{S,i}(r)$ is the coil sensitivity of detection coil i at position r, which is mostly constant over time. In the last step, the magnetic moment has been replaced using $$m(t) = M_{sat} V_{sphere} \hat{m}(t), \qquad (5)$$

where $\hat{m}(t)$ is a unit vector describing the spatial orientation of the magnetization, $M_{sat}$ is the saturation magnetization of the material used (typically between 1.30 and 1.45 T/$\mu_0$ for NdFeB), and $V_{sphere}$ is the volume of the magnetic object.

From (4) it follows that a large dynamic magnetic moment is desirable to induce a high voltage in the receive coils. Since the size of the marker device and, hence, the volume of the magnetic spheres that may be used as the magnetic object and the restoring torque unit, respectively, has to be small in most applications, signal can be increased by using a large oscillation amplitude leading to a large $$\frac{d}{dt}\hat{m}(t).$$

However, the restoring torque does not increase linearly with angle φ (i.e. the amplitude of the oscillation) between restoring field $B_{rest}$ provided by the fixed sphere and magnetization m of the oscillating sphere:

$$|T(\varphi)| = |m \times B_{rest}| = m B_{rest} \sin \varphi \qquad (6)$$

Considering the torque due to friction T=Cφ̇ with damping coefficient C and the torque required for angular acceleration of a sphere with mass $m_s$ and radius $r_s$, T=⅖ $m_s r_s^2 \ddot{\varphi}$, one can set up the equation of motion:

$$m B_{rest} \sin \varphi + C\dot{\varphi} + \tfrac{2}{5} m_s r_s^2 \ddot{\varphi} = 0 \qquad (7)$$

The small angle approximation sin φ≈φ and the replacement m=$M_{sat}V_{sphere}$ leads to $$M_{sat} V_{sphere} B_{rest} \varphi + C\dot{\varphi} + \tfrac{2}{5} m_s r_s^2 \ddot{\varphi} = 0 \qquad (8)$$

The high quality factor of the system allows the further approximation C≈0 and enables calculation of the angular resonance frequency as $$\omega_0 = \sqrt{\frac{5 M_{sat} V_{sphere} B_{rest}}{2 m_s r_s^2}}. \qquad (9)$$

Since the micro-oscillators are typically driven to amplitudes much larger than 10°, this approximation is not valid in the general case. For large angles, the restoring torque is smaller and thus a reduction in frequency occurs, leading to an amplitude dependent frequency $\omega(\varphi_{max})=\omega_0 k(\varphi_{max})$, with $k(\varphi_{max})<1$. The variation in restoring torque during the oscillation furthermore introduces a non-linearity in the sensor response, that is manifested by the existence of higher harmonics of the base frequency in the spectrum.

In addition to the non-linear restoring torque, the force between the two magnetic spheres depends on the mutual orientation of their magnetizations:

$$F(r, m_1, m_2) = \frac{3\mu_0}{4\pi r^4} m_1 m_2 \cos\varphi \qquad (10)$$

For the given sensor design, the force always points along the connecting vector of the two magnetic spheres, however, its magnitude goes to zero at an oscillation amplitude of 90° and even goes from attractive to repulsive at higher angles.

If the excitation fields generated by the transmit coils had a constant amplitude, the oscillation amplitude $\varphi_{max}$ would decrease with increasing distance between coil and sensor (decreasing excitation field) and thus the frequency would decrease. The amplitude also depends on the relative orientation between coils and the sensor as show in FIG. 10.

For a tracking system, orientation and 3D position of a marker device as described herein above needs to be determined. Two independent position determination approaches can be used for localization. In some cases, only one approach may be sufficient, in other situations, a combination of both approaches can be useful to increase accuracy or to identify systematic errors that lead to contradicting results between the two methods.

The first approach may be position determination/localization based on coil sensitivity. This approach makes use of the fact that each coil i in a coil array has a different spatial sensitivity profile $B_{S,i}(r)$ based on its position and orientation.

According to equation (3), a single magnetic oscillator, i.e. a single magnetic object, has a characteristic mechanical oscillation which then creates a response with a characteristic amplitude for each coil that is determined by the respective orientation of the dynamic dipole moment $$\frac{d}{dt}m(t)$$

of the magnetic object with respect to $B_{S,i}(r)$. For reconstruction of sensor position and orientation, a set of forward functions as given by equation (4) needs to be determined.

In the end, a mapping between the 6 position and orientation coordinates of the marker device in the coordinate system provided by the tracking system and the voltage amplitudes at base frequency or higher harmonics for all receive channels is desired. The following equations describe how to get rid of the time dependence in equation (4), so that only amplitudes need to be considered. We start by including all arguments, i.e. position vector r=(x,y,z)$^T$ and orientation vector φ=(φ,θ,ψ)$^T$:

$$u_i(r, \varphi, t) = -B_{S,i}(r) \cdot \frac{d}{dt} m(\varphi, t) = -M_{sat} V_{sphere} B_{S,i}(r) \cdot \frac{d}{dt} \hat{m}(\varphi, t) \qquad (11)$$

The required coil sensitivity profiles can either be calculated from the know coil geometries, measured at defined positions and then interpolated, or be determined in a mixture of both, i.e. a model that can be fitted to the experimental results with adequate fit parameters. For the oscillation of the magnetization, an explicit description for oscillation frequency co and amplitude $\alpha_0$ in the frame of the marker would be $$\hat{m}'(t) = \begin{pmatrix} \cos(\alpha_0 \sin\omega t) \\ \sin(\alpha_0 \sin\omega t) \\ 0 \end{pmatrix} \approx \begin{pmatrix} 1 - \frac{1}{2}(\alpha_0 \sin\omega t)^2 \\ \alpha_0 \sin\omega t \\ 0 \end{pmatrix} = \begin{pmatrix} 1 - \frac{1}{4}\alpha_0^2(1 - \cos 2\omega t) \\ \alpha_0 \sin\omega t \\ 0 \end{pmatrix}, \quad (12)$$

where the prime indicates the local marker frame and the expansions of the trigonometric functions for low oscillation amplitudes $\alpha_0$ have been used. The temporal variation would then be $$\frac{d}{dt}\hat{m}'(t) \approx \begin{pmatrix} 1 - \frac{1}{2}\alpha_0^2 \omega \sin 2\omega t \\ \alpha_0 \omega \cos \omega t \\ 0 \end{pmatrix} = \begin{pmatrix} 0 \\ \alpha_0 \omega \\ 0 \end{pmatrix} \cos\omega t - \begin{pmatrix} \frac{1}{2}\alpha_0^2 \omega \\ 0 \\ 0 \end{pmatrix} \sin 2\omega t, \quad (13)$$

where the first term characterizes the base frequency response and the $2^{nd}$ term characterizes the $2^{nd}$ harmonic frequency response. Using rotation matrices $R(\varphi)$, the magnetizations for general orientation in space can be calculated, i.e.

$$\frac{d}{dt}\hat{m}(\varphi, t) = R(\varphi)\frac{d}{dt}\hat{m}'(t).$$

Thus, starting from (11), the voltage amplitudes for base frequency and $2^{nd}$ harmonic frequency can be determined as $$u_{1,i}(r, \varphi) = -\alpha_0 \omega M_{sat} V_{sphere} B_{S,i}(r) \cdot \begin{pmatrix} \cos\varphi\sin\vartheta\sin\psi - \sin\varphi\cos\psi \\ \sin\varphi\sin\vartheta\sin\psi + \cos\varphi\cos\psi \\ \cos\vartheta\sin\psi \end{pmatrix} \quad (14)$$

and $$u_{2,i}(r, \varphi) = \frac{1}{2}\alpha_0^2 \omega M_{sat} V_{sphere} B_{S,i}(r) \cdot \begin{pmatrix} \cos\varphi\cos\vartheta \\ \sin\varphi\cos\vartheta \\ -\sin\vartheta \end{pmatrix}, \quad (15)$$

respectively. Accordingly, total voltage for coil i would be $$u_i(r,\varphi,t) = u_{1,i}(r,\varphi)\cos\omega t + u_{2,i}(r,\varphi)\sin 2\omega t \quad (16)$$

From the set of forward functions (14) and (15) and the measured response amplitudes, the marker device position and the marker device orientation can be calculated by solving the system of equations using a non-linear solver, which is a standard mathematical method. The accuracy of the solution will improve with the number of receive coils as well as with the orthogonality (i.e. magnitude of differences) between their respective coil sensitivities. The mismatch between 6 unknowns and a higher (or lower) number of receive channels can be taken into account by solving the system of equations in the least-squares sense.

The position determination/localization may also be carried out based on gradient field encoding. While the coil-sensitivity localization is based on the amplitude distribution picked up by the coil array, the frequencies of the marker device or marker devices can be manipulated to give an independent position information. For this purpose, the tracking system may be provided with a control unit which is capable of independently controlling each coil of the coil array, such as to generate a non-uniform magnetic or electromagnetic excitation field, ideally having a constant field gradient over the work space. This may e.g. be achieved by applying low frequency currents to selected coils of the coil array. This additional field changes the restoring field $B_{rest}$ acting on the oscillating magnetic object and thus its frequency (equation 9).

Due to the non-uniform nature of the excitation field, the frequency change will depend on position and orientation of the marker. By sequentially performing the control such as to apply of several encoding fields—e.g. a field gradient applied in 6 different orientations—all three position and two of three orientation parameters of a marker can be determined. The remaining angle can be deferred from the higher order response of the sensing unit of the marker device to the external magnetic or electromagnetic excitation fields, however, at the cost of higher field strengths needed for generating sufficient higher order contributions. The basic encoding idea is related to gradient encoding in MRI; thus, both frequency encoding and phase encoding can be done.

For frequency encoding, the non-uniform field is applied during signal readout to produce the desired frequency offset. For a desired spatial resolution, the applied encoding field strength must be adapted to the frequency sensitivity of the marker device and the frequency resolution the system delivers. Assuming a frequency sensitivity of a NdFeB marker device having a magnetic sphere with a sphere diameter of 0.5 mm as the magnetic object is $$\frac{df}{dB} \approx -50 \text{ Hz}/mT.$$

For a spatial resolution of $\Delta r = 1$ mm and an assumed frequency resolution of $\Delta f = 10$ mHz, a field gradient of roughly $$G = \frac{\Delta f}{\Delta r}\frac{dB}{df} \approx -0.2\frac{mT}{m} \quad (17)$$

would be required. This gradient strength is about a factor of 100 below the gradient of typical MRI systems. Thus, no dedicated water-cooled gradient coils are needed, but the coils of the transmit-receive array can be used for field generation.

For phase encoding, the non-uniform encoding field is applied prior to the signal readout, i.e. the position-dependent frequency offset is only applied for a short window during which a position-dependent signal phase offset accrues. In case that the phase resolution is not sufficient for accurate localization, the duration and/or amplitude of the phase encoding pulses can be varied in sequential excitations, so that ambiguities in phase accruals (larger than 2 pi) can be discerned. Thus, full spatial information is obtained over the course of several readouts. Phase encoding with one non-uniform field pattern (e.g. encoding one spatial axis)

can be combined with frequency encoding with another non-uniform field pattern (e.g. encoding an orthogonal spatial axis) for efficient localization. If a rough marker device position is already known from the sensitivity-encoding approach (which is faster due to its parallel nature), it will suffice to only use few phase-encoding steps that provide the missing high resolution (high spatial frequency) components, but not the complete spatial information.

As described herein below, comparison of localization results obtained with gradient versus sensitivity encoding can be used to identify systematic errors, e.g. resulting from background fields. Furthermore, it should be noted that the linear response to low-frequency external fields of sensors employing two suspended spheres may be suppressed; in that case the higher order response of the frequency can be used for localization or for sanity checks. However, the field sensitivity of these oscillators is much lower so that higher gradient fields will be needed for gradient field encoding.

In the following parameter determination and position determination will be described for closely coupled sensors.

To determine the position (meaning 3 position and 3 orientation parameters) and measure an additional parameter (such as pressure or temperature) is especially difficult if only few coils are used. However, using only a few coils is cost effective and also preferred in some application due to space restrictions. Therefore, it is desirable to modify the detection procedure and hardware in a way to work with only a few coils. One way to do this is to use several marker devices and/or sensors in a coupled fashion. Coupled means here that several sensors/marker devices, each operating at a distinct known frequency, are combined with fixed relative orientation in an assembly. Typically, the sensors are attached to a rigid frame, but technically only the relative positions of the sensors/marker devices need to be known at the evaluation time points.

With enough sensors, the position can be determined with only two coils. This can be easiest seen when comparing to traditional electromagnetic navigation systems. These typically consist of several, usually more than 6, transmit coils and one receive coil which is located and whose orientation is evaluated. However, the rotation of the coil around its axis (axis of the dynamic dipole moment) cannot be detected due to the rotational symmetry of the coil.

In this comparison, the set of rigidly coupled sensors may be viewed as a send array and the single transmit-receive coil as the marker. Thus, it is possible to locate the sensor/marker device array somewhere at a ring around the dynamic dipole axis of the send coil. Note, if the coil is not round the rings are not perfect circles in space but this does not change the argument. So, the position cannot be determined with one coil, but two coils (with non-parallel dynamic dipole moment) the symmetry is broken and the position and orientation of the sensor/marker array can be determined.

The evaluation of the different sensor signals is best done with the complete model approach which is described further below. In brief, a model of each sensor/marker device in the array is generated i.e. in the form of differential equations. This model predicts the sensing units response for a given excitation field. Together with a send/receive system model (including amplifiers, filters and coils) the total response of the array can be predicted. Knowing the excitation pulses in the past (usually only the pulses for several decay times need to be known), the expected receive signal for a marker device position and parameter value can be computed.

It is also possible to incorporate pre-knowledge into this procedure i.e. to allow only a maximum displacement speed of the sensors relative to the coils. Here the only difference to the previous described method is that this process is not done for one sensor but for a set of coupled sensors in an array or for several arrays simultaneously. With the sensor array there is also a set of pre-knowledge available, namely the relative positions and orientations of the sensors/markers in the array. It is especially useful to employ the full parametric approach or at least zero amplitude frequency extrapolation approaches as it is difficult to have all of the many sensors simultaneously operating at the desired amplitude. However, the full model approach is somewhat computational intense. To reduce the needed computing power, it may be beneficial to use first the already explained single sensor/marker evaluation approaches individually and use the results of them as starting values for a final full model-based position and value reconstruction.

In the following some calibration aspects will be explained, wherein firstly it is referred to calibration in the presence of conductive and soft ferromagnetic material.

The presence of conductive and especially soft ferromagnetic material may interfere with the localization by distorting the fields created by the oscillating magnet of the marker or sensor and/or by distorting the field(s) generated by the send coil(s). To a lesser degree, sensor readings may be altered, too, especially as the compensation for amplitude effects could be decreased in accuracy. Therefore, a calibration procedure for the fields is desirable. In addition, it is preferred to also have a measure to identify that field disturbances may happen at the moment. So, first, methods to detect disturbance problems are discussed.

Typically, the tracking system as described herein uses an array of send/receive coils. The coils can be separate send- and receive-only coils or use the same coil for both functionalities. Anyhow, in this configuration, one coil can send and all other coils directly receive the send signal. The receive signal is compared to stored reference values. If the actual received signal deviates too much from the stored values, some action is triggered, like a warning for inaccuracy, triggering a self-calibration process or a suggestion for a calibration process involving user interaction or a combination of these things. It is also possible to send with several coils simultaneously. The send pulse should contain a plurality of frequencies. This can be achieved by generating pulses or by using a frequency sweep or some intermediate, well known in the literature. The frequency analysis is important, as eddy currents running on conductive structures are highly dependent on frequency. So, a significant change may be that the ratio of the received signal at two different frequencies is exceeding some limit. It may also be significant, if at least one spectral component changes by a defined value. However, a uniform change in the whole spectrum may be attributed to a gain change e.g. in the receive amplifier. So, if e.g. receive amplifiers are constructed in a way that gain changes are likely, this effect may be used to set a new gain value in the software to compensate for this gain change. The argument holds in a similar way, if a gain change is expected to happen in the send amplifier but not in the receive path. Here, as a correction, the send amplitude is changed in the computational model (leading to a change in oscillation amplitudes of the sensor, etc.). It is also theoretically possible to measure the impedance of a single coil and use the change in this as an indication for changes in the eddy current environment. However, the capability to measure impedance does not come naturally with the electronics and special equipment is needed. Not only the couplings of the coils can be used to detect environmental changes in the eddy currents, but also known properties of sensors/marker devices in the operation range.

Especially, it is possible to incorporate sensors in the send/receive coil array itself. Even a single sensor/marker is useful. For example, if a single marker is incorporated into the system, at a fixed position relative to the coil(s), a change of the response of the marker is an indication of a changed eddy current environment. It is even more favorable to incorporate a sensor/marker device that is sensitive to low frequency magnetic fields, but not, or only little to other physical properties that could change rapidly. This marker device is not only an indication of a static magnetic field, but of the presence of ferromagnetic material. For detecting ferromagnetic material, the coils will not only be fed with current at frequencies of the sensor/marker device oscillation, but also with a current at a much lower frequency. The current feeding can be done coil by coil or using several coils. If the measured sensor response (i.e. frequency change due to applied low-frequency magnetic field) is not the same as a stored expectation, it is likely that ferromagnetic material distorts the field. If enough coils are present in the system, it is even not necessary to have the field dependent sensor/marker at a known position. With enough coils, the marker device position can be determined using the sensitivity of the coils at the sensor/marker device oscillation frequency and independently by using the sensitivity of the sensor/marker device to near DC magnetic fields (gradient field encoding).

If the positions obtained by the two methods diverge, the eddy current (or ferromagnetic) environment has changed. However, it is even better if not only one such marker device is incorporated into the system, but many. It is also better to have them at known positions than at unknown positions. But it is also useful to have known only some properties of the positions instead of having no position information. A practical way of a partial knowledge is to have sensors/marker devices placed on a rigid structure that ensures a known and time-stable position and orientation relative to each other. Such a calibration "frame" with sensors/marker devices may be placed permanently or from time to time in the operation volume of the tracking system. If the tracking system finds relative positions and orientations that diverge from the expectations, the system is disturbed by eddy currents or ferromagnetic material.

If again, the sensors/marker devices are also sensitive to near DC magnetic fields and the coil array has enough coils, the relative positions of the sensors/markers can be determined independently at very low frequencies where only ferromagnetic material disturbs the fields and at the sensor/marker resonance frequency, where both ferromagnetism and eddy currents lead to field distortions. Hence information about the nature of the disturbing objects can be generated e.g. if ferromagnetic material contributes to the disturbances.

Again, the best approach to detect disturbances is a full mathematical model of the send/receive amplifiers, the coils, and the marker device(s)/sensor(s). This model also includes known positions and orientations, both absolute and relative. In a first step, all positions/orientations and physical parameters are optimized in a way that the errors are minimized. This step includes the pre-knowledge e.g. about the fixed position markers attached to the coil array and the relative positions in potential frames. As a side note, the "frame" does not need to be something introduced only for calibration, but a marker device consisting of many oscillators can act as a frame by itself. In the second step, a total weighted error between expected signals and delivered signals is computed. If the error is over a certain threshold value, it is concluded that some material disturbs the fields. From the nature of the error (i.e. if it occurs on the AC sensitive components or the DC sensitive components) the nature of the disturbing material can be deduced.

Figure 19:
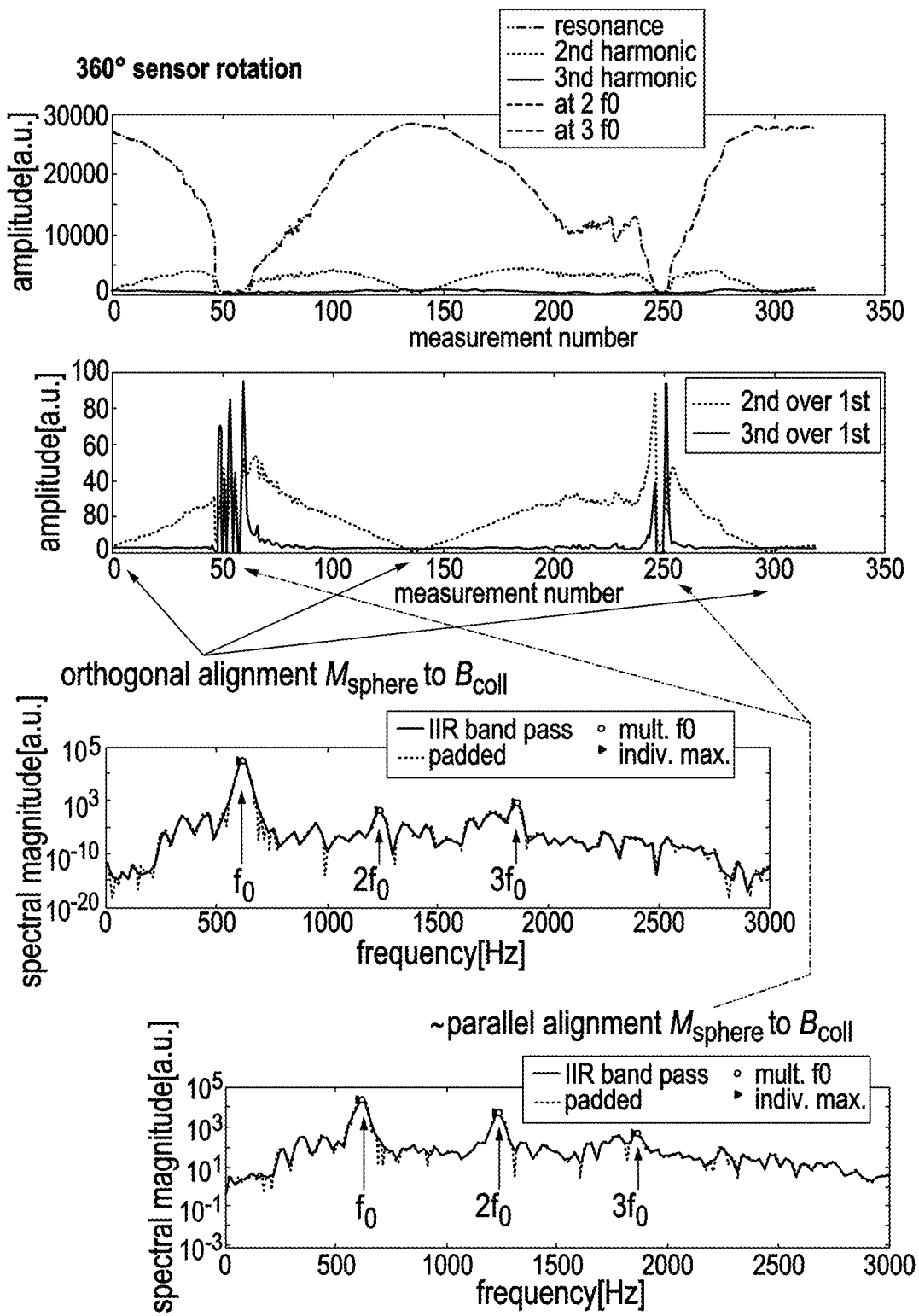
FIG. 19 shows a measured dependence of signal amplitude in different harmonics on sensor orientation with respect to a single transmit-receive coil.

In the following the dependence of the signal amplitude in different harmonics on sensor orientation with respect to a single coil is explained. Specifically, FIG. 19 illustrates a measured dependence of signal amplitude in different harmonics on sensor orientation with respect to a single transmit-receive coil. If the excitation field is aligned parallel to the magnetic dipole orientation, no excitation occurs, and the signal is zero. For orthogonal alignment of field and dipole, the highest oscillation amplitude is achieved. Note that the spatial pattern of the even harmonics is aligned orthogonally to the odd harmonics. This can be seen by the zero of the $2^{nd}$ harmonic amplitude at the orientation corresponding to the maximum in the base signal (Pt harmonic) and $3^{rd}$ harmonic. The amplitude ratio plot (center graph) highlights this difference in orientation dependences: the $2^{nd}$ over $1^{st}$ harmonic ratio goes from zero to a maximum value (or singularity) while the $3^{rd}$ over $1^{st}$ harmonic ratio is flat. The knowledge that the dynamic response at even harmonics is oriented orthogonally to that of odd harmonics can be used to determine the $3^{rd}$ orientation angle of the sensing unit.

It is possible to obtain the position and/or orientation of marker device and hence, of a medical device having the marker device attached thereto—by either sensitivity encoding or by gradient encoding. In some embodiments, a combination of both may be employed.

In the following it will be described how the oscillation amplitude can be determined by using amplitudes of harmonics of the base frequency.

One method to determine the oscillation amplitude is to evaluate the harmonics of the induced signal in the coils. Being non-linear oscillators, the magneto-mechanical oscillators generate harmonics of the resonance frequency in the dynamic dipole moment. These harmonics are picked up in the receive coil(s). Preferentially, care is taken to not suppress these multiples of the base frequency in the sampling and filtering step. The spectrum of the harmonics depends on the details of the sensors. There can be sensors that predominantly generate odd harmonics (at $3\omega_0$, $5\omega_0$, . . . ) and ones that generate even and odd harmonics (at $2\omega_0$, $3\omega_0$, $4\omega_0$, . . . ). However, mixed types can be constructed. The dynamic dipole moment of the odd harmonics tends to align with the dynamic dipole moment of the fundamental frequency, while the even harmonics tend to be aligned perpendicular to the base frequency dynamic dipole moment and perpendicular to the rotation axis. Therefore, the odd harmonics are conceptually the easiest to be used, because the ratio of say the third harmonic's dynamic dipole moment to base frequency's dipole moment is reflected as the corresponding ratio in the recorded voltages in a single coil, e.g. evaluated as spectral peak amplitudes. However, as the amplification in the receive system may be frequency dependent, preferentially a correction is applied to get hold of the true ratio of the 3rd harmonics dynamic dipole moment and the base frequency dynamic dipole moment. This ratio may be measured over a predetermined integration period. For each sensor, a calibration of this ratio to oscillation amplitude or directly frequency shift can be provided and therefore the corrections applied. In the case of the even harmonics, the situation is somewhat more complicated, as the direction of the dynamic dipole moments do not align with the base frequency dynamic dipole moments. So here usually more than one coil needs to be employed or the orientation of the coil to relative to the sensor needs to be determined by other means.

While with a large set of coils (e.g. >=6), both sensor position and orientation can be reconstructed, few coils (e.g. 3-5) should at least allow reconstruction of the orientation of the sensor relative to the coils using similar methods to the positioning determination methods described in detail further below. Then the true ratio of the dynamic dipole moments for even harmonics can be determined using coil sensitivities. The intermediate step of orientation determination can be omitted and a direct map of the ratios of base frequency amplitudes and harmonics amplitudes in the coils can be established using linear algebra methods. It shall be understood that the methods described here in frequency domain can be mapped to methods in other bases like the time domain. In time domain, the frequency analysis is mapped to an oscillation shape analysis. These mapping methods are well known in the mathematical literature.

In the following a determination of the oscillation amplitude based on a time-domain envelope function will be described.

Another way to determine the oscillation amplitude is to utilize the non-linear decay behavior of the signal. The damping of the sensor is usually non-linear. Non-linear decay means that at double stored energy, the average dissipation power of the sensor is not doubled but increased by a factor somewhat higher than two. The reason for this can be the stretching of the filament due to the force modulation described above. Equation (9) shows that at low oscillation amplitudes the attractive force between the magnetic objects are largely constant, but at higher amplitudes they are no more. This force variation depends in first approximation on the square of the oscillation amplitude, corresponding to the approximation of the cosine function by a parabola. This square dependency is the reason for the non-linearity in dissipation. The changing force between the magnetic object periodically stretches the filament(s) which leads to a dissipation contribution. Other effects may as well lead to non-linear behavior. In total these effects lead to the situation that the envelope shape of the decay curve over a given time depends on the initial amplitude. So, if the sensing unit of the marker device has constant initial oscillation amplitude and the distance and/or orientation of the sensing unit of the marker device is changed relative to the receive coil(s), a scaled version of the initial decay envelope is found. However, if the excitation amplitude of the sensing unit is changed, not only the overall amplitude of the decay curve varies, but also its shape. This means that amplitude effects and distance/orientation effects can be disentangled and hence the initial oscillation amplitude can be reconstructed using e.g. a lookup-table of pre-recorded decay curves.

This again leads to the possibility of determining the zero-amplitude frequency or to a controlled constant amplitude excitation as described above. This method only needs a single coil to work. However, it is somewhat sensitive to a movement of the sensing unit during the recording as this also changes the shape of the envelope. Therefore, it is beneficial to incorporate a model of likely sensing unit movements into the evaluation. For example, if it is known that the sensing unit of the marker device will not perform fast accelerations, correcting the decay curve envelope with the assumption of persistent motion is useful.

A determination of the oscillation amplitude based on signal amplitude response to variations in excitation fields will be explained in the following.

Yet another method to determine the oscillation amplitude is to analyze the reaction of the sensor signal to different strengths of the magnetic or electromagnetic excitation field. In this case, the current pulses are systematically varied and the response of the sensor(s) to the different excitation pulses is evaluated. The send pulse current, duration and phase may be varied or a combination thereof. For example, assume that there are two excitation pulses. If the distance is high and the local field amplitude is low, the two pulses are designed to generate twice the amplitude a single pulse would produce. However, if the distance is low and the local field at the sensor is high, the amplitude will be less than twice the amplitude. This results in a characteristic decrease of the receive voltage relative to the expected factor of two. So, the ratio(s) of the receive signal (Fourier) amplitudes of the sensors for a given excitation pattern is a measure of the excitation amplitude and can again be used for extrapolation to the zero amplitude frequency and/or for having a constant excitation amplitude. On top of that, other quantities like the frequency and decay time may be evaluated as well. The ratios of these quantities are also characteristic for the oscillation amplitude and can be used for extrapolation to the zero amplitude frequency.

In the following a determination of a correct parameter based on a full model of all contributing factors will be described.

All the methods described above are just evaluation methods with some methods requiring changes in the transmitted field pulses. No hardware change to the system is needed to do these evaluations. Therefore, it is logical to implement all of them. This may be done my simply running the evaluations in parallel and combining the results in a way to minimize noise, i.e. do a weighted average according to relative noise. While this is relative straight forward and easy to implement, better results can be expected by using a truly integrated mathematical approach that will be outlined below. On the flip side, the mathematically sophisticated approach is considerably more difficult to implement and may need too many computational resources to run on cost-efficient computer hardware. The basis for the correct mathematical approach is a mathematical model for the sensing unit. This model predicts the sensing unit's response to the magnetic or electromagnetic excitation fields and the current sensing unit state. The sensing unit state may be the current deflection angle and rotation speed of the suspended sphere corresponding to the magnetic object.

In some embodiments, also a model of the transmit and receive coils including filter and amplifier characteristics has to be generated. This can be formulated in differential equations, although here a Fourier parameter representation is also not uncommon as long as the transmit and receive systems are sufficiently linear in nature.

Lastly, a model for coil transmit and receive sensitivity needs to be provided. This may be simply a set of spatial points with attached sensitivities and an interpolation algorithm between the points. It could also be based on a simulation of the coils based on the Biot-Savart law. This model can now predict the voltage response of the sensor at any given location and orientation with the given history of excitation pulses and external parameters. So, the procedure is to vary sensor position and orientation and the sensor influencing physical parameters in the simulation in a way that the recorded signal and the simulation match in the best possible way. Many well-known optimization methods may be used, such as gradient descent or random walks. The match may be defined as the root mean square of the sum of the difference of the measured sample points and the simulated sample points. The match is best if this quantity is lowest. The best fit may be altered introducing additional constraints, e.g. by a model of the expected relative positions and orientations or by a constraint on the maximal expected sensor accelerations and/or a model of the measured quantities, which for instance give a constraint on the maximal rate of change in these quantities. Additional sensor input may be used as well, like accelerometers on a hand-held coils system for at least one independent input of distance and orientation changes. As the full model-based evaluation processes are computationally intensive, they can be combined with one or several of the previous methods to give a good starting point for further optimization.

The processor can also be configured to compensate for gravitational effects as it will be explained in the following.

The processor and, more particularly, the position determination unit can also be configured to compensate for earth magnetic field and other static field effects.

Static background fields add to the field of the fixed magnetic object and thus modulate the restoring field $B_{rest}$ seen by the oscillating magnet. This changes resonance frequency according to equation (8) and is therefore a source of error for sensing via the oscillator's frequency changes. For magnetic spheres of diameter 0.5 mm made from NdFeB with a saturation magnetization of $1.3$ T/$\mu_0$, the fields created by the fixed sphere at the center of the oscillating sphere are 16.1 mT and 6.8 mT for center-to-center distances of 0.75 mm and 1.0 mm, respectively. Earth magnetic field is between 25 and 65 µT. The frequency difference between parallel and antiparallel alignment of the static field component with the maximum earth magnetic field of 65 µT would create a frequency difference of about 5 Hz and 9 Hz for the above distances of 0.75 mm and 1.0 mm, respectively. Different mitigation strategies to this are introduced in the following.

A mitigation on the marker device side is the use of the design employing two suspended spheres with identical magnetic dipole moment and moment of inertia (or a suitable ratio of the two quantities) as the magnetic object instead of a single sphere that has been previously described as the magnetic object. Since the counter-oscillation occurs at a single frequency, the first order effect of a static bias field like the earth magnetic field is cancelled.

Another mitigation strategy is to use absolute field sensors in the system to measure magnitude and orientation of static background fields. Based on the sensor orientation determined using the methods discussed previously, a frequency or field correction can be calculated to arrive at an improved position determination. For sensing static background fields, any magnetic field sensor with sufficient sensitivity and a footprint that can be integrated in the tracking system can be used. One cost-efficient choice could be 3-axis Hall sensors. An alternative would be a 3-axis array of temperature-compensated micro-bots with a well-defined zero-field frequency.

From the change to their respective frequencies, the magnitude and orientation of the background fields can be determined. Ideally, their resonance frequencies are chosen such that they do not interfere with the frequency of the sensing unit of interest. Instead of correcting for the frequency offset in the evaluation, one can also use the coils of a multi-coil tracking systems to generate small offset fields to counter-balance the earth-magnetic and other background fields. If inhomogeneous fields exist in the field of view due to the presence of ferromagnetic material, several sets of 3-axis magnetic field sensors can be employed to characterize the spatial field variations.

The marker devices should have a high quality factor and need to have a large frequency sweep to be sensitive to the measured quantity over the range required for a specific application. The high quality factor is especially important at high oscillation amplitudes where the highest signal is generated. As the two magnetic objects have strong attractive forces, and the forces strongly increase with shrinking distance (to the 4th power of the distance, cf. equation (9)), both properties may be worsened. The strong forces lead to a relatively strong tension in at least one filament holding at least one magnetic object. This tension itself does not lead to a dissipation path. However, especially at large oscillation amplitudes, the forces between the magnetic objects are reduced and thus the tension on the attachment portion is periodically reduced. This results in a periodic lengthening and shortening of the attachment portion which may usually result in heat generation. Hence, power is extracted from the oscillator. The forces also depend strongly on the distance of the magnetic objects and become very large if the objects get close to each other.

To solve this problem, a method to reduce the force and the change of the force is described. It consists just of a portion of magnetic material that is magnetized in the opposite direction next to the other magnetic object, as shown in FIG. 20.

Figure 20:
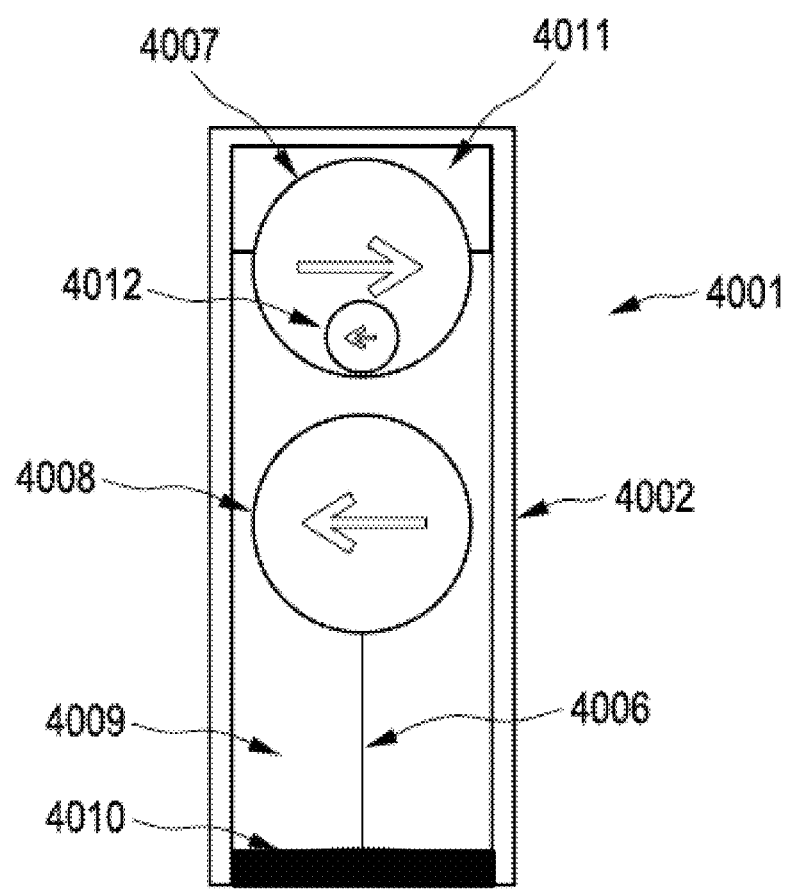
FIG. 20 shows schematically and exemplarily a further embodiment of a marker device.

In FIG. 20, the sensing unit 4001 comprises a magnetic object 4008 being a permanent magnet suspended via an attachment portion 4006, such as a filament which is preferentially a high strength wire, from a hard wall 4010 of a casing 4002. The hard wall 4010 is preferentially made of a metal or a polymer that is insensitive to external pressure influences. Further, also the remaining part of the casing 4002 might be made of metal or of a polymer. The casing 4002 might be filled with gas or it might provide a vacuum space. A further magnetic object 4007 is fixed via glue 4011 to an inner end surface of the casing 4002. The two magnetic objects 4007, 4008 are generally magnetized in opposite directions. However, the fixed magnetic object 4007 also comprises a part with a reverse magnetization orientation 4012.

So, if two magnetic spheres are involved, in this example at least one sphere obtains a cap magnetized in opposite direction. The cap is located next to the other magnetic sphere. If one sphere is fixed and the other one is oscillating, it is best to have the cap on the fixed sphere. In this way, the dynamic dipole moment of the sensor is not reduced. Only the oscillation frequency is slightly lower. However, it is also possible to reverse the roles of the spheres. The oppositely magnetized portion is so small that at all operational distances, the net force between the magnetic objects is still attractive. If the reversely magnetized portion is small enough, the attraction condition can be meet right until touching of the magnetic objects.

There are several ways to make the reversely magnetized caps. One is to just add some magnetic material on top of at least one magnetic object. The magnetic material can be magnetically soft or magnetically hard. It can be a solid continuous magnetic object or a magnetic paint or something in between. The magnetic material tends to align in a way to form the opposite magnetization by itself. In addition, it also tends to stick to the magnetic object. Nevertheless, this additional material should be glued to the magnetic object especially if the two main magnetic objects can touch each other occasionally. To keep the originally desired shape, some material may be removed from the magnetic object to be altered, e.g. by grinding.

There is an alternative way to form the reversely magnetized zone. It can be created just by reversely magnetizing the desired zone of the magnetic object. This could be achieved by strong pulses of current through a conductor near the magnetic object. However, this is not very practical due to excessive heating. It can be achieved easier by just heating the affected portion of the magnetic object to near or above the Curie temperature. This will result in the reversal of the magnetization. The effect can be augmented by applying a pulsed or constant magnetic field in the reverse direction. The fields can also incorporate strong gradients by using some hard or soft magnetic material near the zone to be affected. As the heating has to be fairly localized, the temperature increase needs to be very rapid, so that the total energy deposited into the magnetic object is low and does not bring it near Curie temperature as a whole. A suitable heating source could be a laser. Resistive or inductive heating methods may work as well.

Further, some approaches to determine the presence of field disturbances may also be a good starting point for methods to compensate for the effects of the field disturbances. On such exemplary method can be easiest illustrated when assuming that conductive material causing eddy currents is present, but not ferromagnetic material. When applying the model described above, it is possible to get the right positions from the evaluation of the near-DC dependent signals (gradient field encoding), but the wrong positions and local field amplitudes at the sensor frequency and its harmonics (coil sensitivity encoding). Therefore, it may be possible to distort the higher frequency fields in a way to match the expectations. After the distortion is applied, all positions and sensing unit read outs will be improved. It is beneficial not to solely rely on the position evaluation based on the near DC magnetic fields, because the AC sensitivity encoding is much faster.

The most critical part for this compensation method is to determine the right model for the distortion of the AC field. A simple solution is to parameterize a field shift function e.g. using simple 3D polynomials. This means that the field value is not used of the actual position, but of the position transformed by the 3D polynomials. This is computationally efficient but may lack physical insight and it is not apparent, how e.g. the measurements of the coil couplings could be incorporated into this framework. So, it is better to use models that are closer to the physical reality. For example, it is better to use the field model of conductive plates near the coil system to induce the desired field distortions.

So basically position, angle thickness, and size of some virtual plates are varied until the model expectations and the measured data match. How to model such conductive plates is well known in the electromagnetic simulation literature. This type of modeling has the additional advantage that it is easy to incorporate the shapes of objects that will likely occur in a specific environment. So, if a special device is brought close to the field of view, e.g. an X-ray C-arm, this device is known and can be modelled before, so that only the exact orientation and position has to be optimized by the system software. A further advantage is that the assumed disturbing object position can be displayed by the system or the data is transmitted to a second system that does the display task. In this way, the user can be specifically pointed to objects that disturb the measurement and the user may want to move or remove them. During this process, the coupling data of the coils act essentially as an array of metal detectors. The incorporation of ferromagnetic material is conceptually the same as with the conductive material that produces eddy currents. However, ferromagnetic material simulation is a computationally a little more intense and as there may be a lack of definite reference positions defined by dedicated marker devices, it may not result the exact position. But again, it is best to model a set of ferromagnetic material, like sheets and rods and place and deform them in simulation around the coil array. Here it is very beneficial for the model if a database of likely ferromagnetic objects is provided. In addition, the process of mutual coupling measurements could be augmented by the measurement of harmonics generation in the coil environment. The presence of harmonics is a strong indication for soft ferromagnetic material and the measured signals give valuable input for the size and position of the objects.

In the following an excitation pulse generation will be described.

The tracking system, and, optionally, the field generator preferentially comprises software to generate the timing and shape of the excitation pulses. This excitation pulse generator is preferentially aware of the capability of the hardware. There are different types of amplifiers and filtering possible. One type of amplifier is capable of generating a current waveform that closely follows a rather arbitrary path. These are here called "analog amplifiers".

The other is only capable of increasing the current at a predefined rate, decreasing it at a similar rate, and letting it more or less constant. In essence, these amplifiers apply a voltage with positive or negative sign at the coil or act as a short circuit. These are here called "digital amplifiers". The digital amplifiers can have different switching speeds i.e. allowed number of state changes per unit time. If the switching speed is much higher that the oscillation speed, the digital amplifier again acts like an analog amplifier. Hence, this type of amplifier can be conceptually treated as an analog amplifier.

If the switching speed is only about the same as the marker device oscillation frequency, the treatment has to be a little different. However, this is the more difficult situation, therefore all the discussion will focus on that. This type of amplifier has some benefit over the analog ones. The main benefit is that the efficiency of this amplifier is usually very high and a 98% efficiency is readily achieved. A further advantage is that interfacing with the computing system is very easy. Between amplifier and coil, a matching circuit could be present. The simplest matching circuit is just a capacitor in series to the coil. Using the matching circuit, the maximum current through the coil at a given amplifier supply voltage increases. Such a matching circuit however has the drawback of blocking low frequency currents.

Some sequences may require low frequency currents. Solutions to this problem can be twofold. First, a matching circuit can be provided that is transparent at high and low frequencies. An example of such a circuit would be a coil or coil capacitor series circuit parallel to the first matching capacitor. The other way is to have a switch that bypasses the matching circuit and when near DC current is needed, the switch is closed. In the bypass path, a capacitor can be integrated, too, if the resonance frequency is low enough. In the same way, a whole series of different matching frequencies can be provided using a multitude of switches and capacitors. Also, note that even if the circuit is tuned to near DC, some current at the marker device frequency is still available. It shall be noted, that it is not necessarily possible to use the DC currents during read-out. There are two main elements to provide this capability. First, the DC currents are not allowed to interfere with the reading. There is manly a problem if the send and receive coils are combined. The DC source can provide a short circuit path to the signal. This has to be avoided and the proper matching circuit avoids it.

The matching circuit has to introduce a sufficiently high impedance between the coil and the DC source. This can be achieved by an additional coil in series with an inductivity on the order of the send/receive coil inductivity. The inductivity may have a parallel switch to short it if it is not needed. There are many other solutions available. Second condition is that the DC source does not introduce too much noise i.e. the current source noise does not prohibit the accurate measurement of the marker devices. This can be achieved by a suitable analog filter in the DC send case.

This filter may be a bypassed during AC send pulses by a suitable switch (MOSFET opto-couplers for example). It may also be feasible to avoid switching action in the DC source during signal receiving altogether and just use the slowly decaying current in the coil. It may be also feasible to do only a few switching actions while receiving and just dismiss the received data when they are corrupted. The DC field sources may be also entirely separate coils or the field generators may be (moving) permanent magnets. This avoids most problems. An additional issue with the presence of DC currents during signal reception is that the coils may provide a different environment for the sensors. This means, that for example some coils can be shortened for AC currents and the AC field do no more penetrate the coils changing field values in nearby coils. This effect has to be taken into account when computing positions and/or orientations. Two main field elements interact with the marker device. One is the near DC amplitude of the current i.e. a current value averaged over a time in the order of 0.1 seconds (about 0.01 seconds to about 1 second). The other is the Fourier amplitude (as a complex value, as the phase is important) at the resonance frequency of the sensors/markers. Therefore, the first task is to map the two values to the generation of the sequence.

In the following a mapping if desired Fourier amplitudes and currents to a specific time-domain pulse pattern will be described.

It is also useful to generate a software sub-system that does this exact type of mapping i.e. a piece of software that gets the desired near DC currents and the desired Fourier amplitude (and frequency) as an input and that generates the time-domain pulse sequences. It is also desired that this software returns the information whether the desired values can be reached within the limits imposed by the hardware, like maximum currents or maximum heating of coils or regulatory limitations, e.g. patient heating or peripheral nerve stimulation. Instead of a simple yes/no information, an information about the severity of the undesired side effects may be provided. This information may be provided per individual send cannel (per send coil). A further return value may be the actual best-fit output DC current and Fourier amplitude(s). The input may not only be one frequency and Fourier amplitude combination, but also a variety of Fourier amplitudes at different frequencies. The maximum length of the pulse sequence may also be a parameter that is an input for this function. The inner workings of are as follows: In the case of analog amplifiers, a first result may be generated simply by doing the inverse Fourier transform of the desired Fourier amplitudes (and DC values) for the desired send time. If this process results in a wave form that cannot be realized due to some limitations, this is reported back and may be a scaled version is scheduled for generation. The possible filter characteristics is accounted for by the appropriate convolution. If there are several switched filter states, all may be tested and the one with the lowest demand on the amplifier may be chosen. Note that there are several heuristics available, so that for most cases not all filter states have to be evaluated. It is for example possible to omit filters with far off resonance frequencies, if better ones are available. For the digital amplifier, the inverse Fourier transform (including filter effects) gives a good starting point for optimization. In this first approximation step, the resulting peaks in the time spectrum are approximated by two (or at best a few) ramps and flat regions in between. So, for example a half period of a sine wave starting with zero and ending with zero is approximated by first a flat (zero) portion, then a ramp up, then a flat portion, then a ramp down, and finally a flat (zero) region. The timing of the different portions is arranged in a way to reach approximately the same area. After this first approximation, a second step, where the positions of the ramp and flat part beginnings are shifted to reach a fest fit with the desired Fourier values. The best fit may be the least sum of squares of difference (complex) values of desired and achieved Fourier components. All the usual optimization algorithms, like gradient descent, can be used.

In the following a mapping of desired Fourier values at marker devices to currents in coils will be described.

The next higher abstraction level of the pulse generation program is the software piece that demands specific field Fourier values and directions at a specific position as an input and translates them to the demands for the currents in the coil. The evaluation algorithm usually provides some measure of position and orientation of the sensors/markers. The position is not and does not need to be a position in 3D space. However, a 3D position is the ideal case. For example, if only one coil is present, it may be only possible to determine the field value in sensitive direction at the sensor. Nevertheless, this also translates into some virtual position and orientation in 3D space. Therefore, these situations do not need a special handling in the software. The translation to the demands for coil currents are then the result of an optimization process. There is a model that computes from currents in the coils Fourier field components at specific spatial positions. This is the basis for an optimization, where coil current Fourier components are optimized in a way to generate the desired field components. There is usually not an unambiguous way to form the desired fields out of coil currents. It may also be the case that the desired currents are not compatible with the restrictions in the hardware system. The lower level software returns values describing the negative effects and the software uses this information to optimize the currents. The optimization has the goal to have a good compromise between achieved field Fourier components at the marker devices and the negative effects. This means that the deviation from the desired fields and the side effects are combined into one number and for this number a maximum or minimum is found using standard optimization algorithms. The combination of the number may be a weighted sum of squares. Naturally for this entity a huge number of working mathematical combinations can be found. Finally, this part of the program returns the calling program (higher level) the achieved fields at the positions and the quality values for it to do its optimization.

In the following a generation of desired field Fourier values for the markers/sensors will be described.

At this level of abstraction, the software system actually deals with the measurements that need to be done. So, the input for this program is the current demand of what things shall be measured how accurately and how fast. These requirements depend on the actual application the sensors/ markers are used and therefore are not part of this document. The requirements could be very different. For example, if only a single sensor is involved, the requirement would be for example measure the single quantity as accurately as possible every say 0.1 seconds. If the application is a tracking solution with multiple coupled markers, the desired outcome may be that say every 0.1 seconds a position update is made for the whole marker assembly regardless of which of the markers/sensors in it contribute to the signal (based on coil sensitivities) and that every 1 second an independent position check with the gradient method is demanded. This program also has access to the current state of the sensors/markers (position/oscillation parameters etc.) and the simulation model described elsewhere in this document. From this, the optimal excitation field Fourier values including direction for each marker device can be computed. These parameters can be passed to the previously described lower software levels (with a wanted execution somewhere in the future) to ultimately generate the currents. In the case of the single sensor, this would work immediately and the plan can be written to the hardware output buffers. However, for the tracking of a marker device assembly for example, there exists likely no pulse shape that excites all individual marker devices perfectly. Especially the phase would be not suitable for all the individual marker devices. Therefore, the software may have to try to concentrate the optimal excitation to just a sub-set of the marker devices present and try to find a solution which gives working pulse sequence. This is the general working principle of the optimization of this software. It tries to change the desired excitation of the various sensors and focusing on a few to still get the desired outcome. The conceptually simplest approach is to go through all possible sub-sets of marker devices and check which sub-set of excitation gives the best information on the desired parameters. As there are many sub-sets possible, the program needs to add some heuristic methods to reduce the complexity. For example, it can be first observed what other marker devices are excited too, if a given one is excited and these can be always grouped together. If a suitable solution is found, it can be written to the output buffer. The inclusion of near DC magnetic fields may need an additional logic depending on the hardware implementation. If the hardware is capable of applying DC magnetic fields, while the signals are recorded, the software does not have to do something very special, except applying one or several gradients during read-out. However, if DC gradients and read-out are incompatible, there is an additional optimization step needed, that produces the right DC field or gradient at some time in between excitation pulses. The logic behind the optimization remains the same. Parameters are varied until the simulation predicts a good enough measured value for the application.

A start-up sequence generation will be described in the following.

The algorithm generally assumes that there is already quite some knowledge about the marker devices available to optimize the sequence. Usually, at the start of the sequence, this is not available in full. For example, from the application it could be known how many marker devices should be present in the application and in which range the frequencies could be. But the exact frequencies and positions would not be known. Therefore, a special start-up sequence is needed that tries to find all possible marker devices at all possible positions. The simplest possible start-up sequence is as follows. The working volume is split into a spatial 3D or abstract grid. The abstract grid is the grid to use if there are not enough coils to do a full 3D encoding. Each spatial point is split into different directions. The program goes through each position and each angle at the position and applies the highest send power for a given frequency and a pre-set send time. Then the system records the potential signals from the sensors/markers. Usually, one send pulse excites not only one marker device but also many others simultaneously. However, this procedure ensures that even the marker device with the weakest possible signal will be detected, too. An optional next step is to excite each sensor individually with different amplitudes. From this, the non-linear properties can be extracted. A further optional step is to excite each marker device in the presence of a DC field or a measure the signal phase after a DC field (again in various directions) to determine the sensitivity of the marker devices to DC magnetic fields. These basic procedures can be sped up tremendously by using some knowledge about the system. For example, it is likely that, if a faraway volume is already searched for a sensor/marker, many or all nearer volumes received the highest possible amplitude at least for some angles. Therefore, only the few remaining parameters need to be applied for the nearer volumes. The same logic can be used for assessing the non-linear character of the sensors/markers or their response to DC magnetic fields.

In the following strategies for high temporal resolution measurements are explained.

For many applications, it is desirable to have a high temporal resolution. So, strategies are desired to reach a high temporal resolution with the magneto-mechanical oscillators, for both, position as well as parameter determination. The simplest approach for a high temporal resolution is to simply decrease the repetition time. Repetition time means the time period between subsequent excitation pulses. After each excitation pulse, the frequency and amplitudes are determined from which the physical values and position can be computed, as described elsewhere. However, the quality factor of the marker devices tends to be relatively high and the oscillation amplitude has not declined much at the time of the next excitation pulse. To always get the desired marker device excitation, the phase of the next excitation has to be considered. Usually, we want an "in phase excitation", i.e. an excitation in a way that the marker device gains energy right from the start of the excitation pulse. How the timing is optimized is described elsewhere. The in phase excitation minimizes the send energy and hence the excitation pulse length can be kept to a minimum. This increases overall signal to noise ratio.

The high repetition rate has some drawbacks. First, during and shortly after the excitation pulses, the system usually cannot receive values and hence the signal to noise ratio may not be optimal. Secondly, each send pulse destroys some knowledge about the phase of the sensors' oscillation. Only if the excitation pulse and sensor orientation are kept tightly controlled and are precisely known, the phase information can survive to some degree, however this is technological challenging. The phase information over a longer period may be useful, as in it, information about the average frequency (hence average physical quantity) is encoded. The measurement of an average physical quantity is considerably more accurate when evaluating a double length interval than just doing the evaluation of the first half and the second half independently and averaging the two results. Therefore, it may worthwhile to have not as many excitation pulses as measurements but extract from one signal pulse more than one measured value. This can be done simply by splitting the signal in several sub-sections and evaluating each subsection individually.

This simple approach does not take into account that the measurements become better, if a longer data set is used. To incorporate this, the set can be split into a hierarchy of sub sets and every sub-set in every hierarchy is evaluated and the averages are scaled to match the longer data sets. So, for example a data set (one unperturbed decaying signal) is first evaluated as a whole. Then it is split into two, and the two split data sets are separately evaluated. Then to each result the same number is added so that their average matches the average of the full set. This process can be repeated to have 4, 8 and so on sub-sets in the end. This approach may be refined mathematically to a full model-based evaluation. For this, a model of the evolution of the physical parameter is generated (and possibly also including the spatial movement of the sensor). This model may be a polynomial of a certain degree or some other suitable mathematical function. The function should describe the physical nature of the measured quantity in a way so that only a low number of parameters needs to be used. So, for example when the parameter is the blood pressure, the model may be better a Fourier series, because this describes the pressure wave form of heart beats better than polynomials. Then the parameters are varied to match the measured data set as good as possible. If discrete measurement points are needed in the end, they can be simply computed using the output of the model for certain time points.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Determinations like the determination of the resonance frequency based on the induced signal, the position and/or orientation signal determination based on the resonance frequency, the determination of a calibration curve et cetera performed by one or several units or devices can also be performed by any other number of units or devices. The control of the tracking system can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention relates to a tracking system and a marker device, the tracking system used for tracking the marker device and the marker device adapted to be attached to a medical device. The tracking system is provided for use during surgery, whereby the marker device comprises a sensing unit comprising a magnetic object providing a permanent magnetic moment, wherein the sensing unit is configured to transduce an external magnetic or electromagnetic excitation field into a mechanical oscillation of the magnetic object and wherein the tracking system comprises a field generator for generating a predetermined magnetic or electromagnetic excitation field for inducing mechanical oscillations of the magnetic object of the sensing unit, a transducer for transducing a magnetic or electromagnetic field generated by the induced mechanical oscillations of the magnetic object into one or more electrical response signals and a position determination unit for determining the position of the marker device on the basis of the one or more electrical response signals.

The invention claimed is:

1. A tracking system for use in surgery, the tracking system comprising:
    a field generator for generating a predetermined magnetic or electromagnetic excitation field for inducing mechanical oscillations of a magnetic object of a sensing unit of a marker device, wherein the magnetic object provides a permanent magnetic moment, wherein the sensing unit is configured to transduce the predetermined magnetic or electromagnetic excitation field into induced mechanical oscillations of the magnetic object, wherein the induced mechanical oscillations of the magnetic object generate a magnetic or electromagnetic response field;
    a transducer for transducing the magnetic or electromagnetic response field generated by the induced mechanical oscillations of the magnetic object into one or more electrical response signals, and
    a position determination unit for determining the position of the marker device on the basis of the one or more electrical response signals.

2. The tracking system of claim 1, wherein the position determination unit is adapted to determine, on the basis of the or more electrical response signals, at least five degrees of freedom for the marker device relative to a coordinate system provided by the tracking system, the at least five degrees of freedom including a position and at least two orientation angles of the marker device relative to the tracking system.

3. The tracking system of claim 1, wherein the tracking system is adapted to determine the position of a plurality of marker devices, each of the plurality of marker devices comprising a respective sensing unit;
    wherein the magnetic objects of the respective sensing unit are oscillatable with different resonance frequencies such as to generate a different magnetic or electromagnetic response field to be transduced in respective one or more electrical response signals specific to the respective marker device,
    wherein the position determination unit is adapted to determine the position of one or more of the plurality of marker devices based on the respective one or more electrical response signals.

4. The tracking system of claim 1, wherein the tracking system is configured to compensate a dependence of the one or more electrical signals on a temperature.

5. The tracking system of claim 1, wherein the position determination unit is configured to apply a compensation algorithm in order to compensate for one or more of:
    static background fields, and
    dynamic background fields.

6. The tracking system of claim 1, wherein the position determination unit is configured to apply a compensation algorithm in order to compensate for non-linearity resulting from different oscillation amplitudes of the mechanical oscillations.

7. The tracking system of claim 1, wherein the field generator comprises a magnetic field generation array comprising a plurality of generation units arranged in a predetermined spatial arrangement,
    wherein the one or more electrical response signals are indicative of a characteristic mechanical oscillation of the magnetic object of the sensing unit induced by each of the plurality of generation units, wherein the position determination unit is adapted to determine the position of the marker device at least partially based on the one or more electrical response signals being indicative of the characteristic mechanical oscillation.

8. The tracking system of claim 7, wherein the position determination unit is adapted to determine, from the one or more electrical response signals, an amplitude of the characteristic mechanical oscillations of the magnetic object for each one of the plurality of generation units.

9. The tracking system of claim 1, further comprising a control unit, and wherein the field generator comprises a or the magnetic field generation array comprising a plurality of generation units arranged in a predetermined spatial arrangement;

wherein each one of the plurality of generation units is adapted to be controlled independently of the remaining ones of the plurality of generation units by the control unit, the control unit being adapted to control at least some of the generation units such that at least one spatial excitation field component of the magnetic or electromagnetic excitation field is modifiable by said control;

wherein the position determination unit is adapted to determine the position of the marker device at least partially based on the one or more electrical response signals being indicative of the modifying of the at least one spatial excitation field component.

10. The tracking system of claim 1, wherein the field generator is adapted to sequentially generate a set of different additional magnetic or electromagnetic encoding field varying in space and/or time;

wherein the position determination unit is adapted to determine the position of the marker device at least partially based on the one or more electrical response signals transduced by the transducer based on a magnetic or electromagnetic field generated by the induced mechanical oscillations of the magnetic object in response to each of the set of different additional magnetic or electromagnetic encoding fields.

11. A medical tool for use by medical personnel, and a marker device attached to the medical tool, wherein the marking device includes a casing, and a sensing unit comprising a magnetic object providing a permanent magnetic moment, wherein the sensing unit is configured to transduce an external magnetic or electromagnetic excitation field into induced mechanical oscillations of the magnetic object, wherein the induced mechanical oscillations are independent of an external pressure to which the sensing unit is subjected, wherein the induced mechanical oscillations generate a magnetic or electromagnetic response field, wherein the medical device has a longitudinal shape and is adapted to have a plurality of marker devices claim 10, wherein the plurality of marker devices are arranged along a longitudinal axis of said medical device.

12. A tracking method for tracking a marker device, wherein the marker device includes, a casing, and a sensing unit comprising a magnetic object providing a permanent magnetic moment, wherein the sensing unit is configured to transduce an external magnetic or electromagnetic excitation field into induced mechanical oscillations of the magnetic object, wherein the induced mechanical oscillations are independent of an external pressure the sensing unit is subjected, and wherein the induced mechanical oscillations generate a magnetic or electromagnetic response field, and the marker device is configured to be attached to a medical device using a tracking system claim 1, the tracking system being configured to be used during surgery;

wherein the method comprises:

generating a magnetic or electromagnetic excitation field for inducing the induced mechanical oscillations of the magnetic object of the sensing unit, transducing the magnetic or electromagnetic response field generated by the induced mechanical oscillations of the magnetic object of the sensing unit into one or more electrical response signals, and determining a position of the marker device on the basis of the one or more electrical response signals.

13. A non-transitory computer readable medium configured to store a computer program, the computer program comprising machine executable instructions for causing a tracking system to track a marker device being attached to a medical device, wherein the marker device includes: a sensing unit comprising a magnetic object providing a permanent magnetic moment, wherein the sensing unit is configured to transduce an external magnetic or electromagnetic excitation field into-a induced mechanical oscillations of the magnetic object, and wherein the induced mechanical oscillations generate a magnetic or electromagnetic response field; and wherein the tracking system includes: a field generator for generating a predetermined magnetic or electromagnetic excitation field for inducing the induced mechanical oscillations of the magnetic object of the sensing unit; a transducer for transducing the magnetic or electromagnetic response field generated by the induced mechanical oscillations of the magnetic object into one or more electrical response signals, and a position determination unit for determining the position of the marker device on the basis of the one or more electrical response signals, to carry out the tracking method of claim 12, when the computer program is run on a computer controlling the tracking system.

14. A marker device configured for being attached to a medical device, the marker device comprising:

a casing, and a sensing unit comprising a magnetic object providing a permanent magnetic moment, wherein the sensing unit is configured to transduce an external magnetic or electromagnetic excitation field into induced mechanical oscillations of the magnetic object, wherein the induced mechanical oscillations are independent of an external pressure to which the sensing unit is subjected, and wherein the induced mechanical oscillations generate a magnetic or electromagnetic response field.

15. The marker device of claim 14, wherein said casing is a hard casing.

16. The marker device of claim 14, wherein the marker device has an elongated shape with a maximum dimension being smaller than or equal to 5 mm and a minimum dimension being smaller than or equal to 1 mm.

17. The marker device of claim 14, wherein the magnetic object is arranged within the casing such as to be rotatable out of an equilibrium orientation if the external magnetic or electromagnetic excitation field is acting on the magnetic object; and wherein the sensing unit further comprises:

a restoring torque unit for providing a restoring torque to return the magnetic object back into the equilibrium orientation if the external magnetic or electromagnetic excitation field has rotated the magnetic object out of the equilibrium orientation such as to allow the mechanical oscillations of the magnetic object with a resonance frequency.

18. A medical device including a tool for use by medical personnel, and a marker device attached to the tool, wherein the marking device includes a casing, and a sensing unit comprising a magnetic object providing a permanent magnetic moment, wherein the sensing unit is configured to transduce an external magnetic or electromagnetic excitation field into induced mechanical oscillations of the magnetic object, wherein the induced mechanical oscillations are independent of an external pressure the sensing unit is subjected to, wherein the medical device has a longitudinal shape and is adapted to have a plurality of marker devices claim 14, wherein the plurality of marker devices are arranged along a longitudinal axis of said medical device.

19. A medical device for use during surgery, the medical device comprising:
 a tool for use by medical personnel, and
 a marker device attached to the medical tool, wherein the marking device includes;
  a casing, and
  a sensing unit comprising a magnetic object providing a permanent magnetic moment, wherein the sensing unit is configured to transduce an external magnetic or electromagnetic excitation field into induced mechanical oscillations of the magnetic object, wherein the induced mechanical oscillations are independent of an external pressure to which the sensing unit is subjected, and wherein the induced mechanical oscillations generate a magnetic or electromagnetic response field.

20. The medical device of claim 19, wherein the medical device comprises a tip adapted such as to have the marker device attached thereto.

21. The medical device of claim 19, wherein the medical device comprises one or more of an interventional device or an implant, in particular an electrical implant and/or an orthopedic implant.

22. The medical device of claim 19, wherein the medical device comprises one or more of: a surgical instrument, an imaging probe, an endoscope, a bronchoscope or an ingestible pill.

23. The medical device of claim 19, wherein the medical device comprises one or more of a catheter, a wire, in particular a guidewire, a stent, one or more aneurism coilings, one or more vena cava filters, a heart valve, a shunt, a needle, a wire, a tube, a stylet or a radioactive seed.

* * * * *